(12) United States Patent
Lücking et al.

(10) Patent No.: US 8,735,412 B2
(45) Date of Patent: *May 27, 2014

(54) SULFOXIMINE-SUBSTITUTED ANILINOPYRIMIDINE DERIVATIVES AS CDK INHIBITORS, THE PRODUCTION THEREOF, AND USE AS MEDICINE

(75) Inventors: Ulrich Lücking, Berlin (DE); Rolf Jautelat, Haan (DE); Gerhard Siemeister, Berlin (DE); Julia Schulze, Berlin (DE); Philip Lienau, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 244 days.

This patent is subject to a terminal disclaimer.

(21) Appl. No.: 13/125,066

(22) PCT Filed: Oct. 9, 2009

(86) PCT No.: PCT/EP2009/007247
§ 371 (c)(1),
(2), (4) Date: Aug. 8, 2011

(87) PCT Pub. No.: WO2010/046035
PCT Pub. Date: Apr. 29, 2010

(65) Prior Publication Data
US 2011/0294838 A1   Dec. 1, 2011

(30) Foreign Application Priority Data

Oct. 21, 2008 (EP) ..................... 08167113

(51) Int. Cl.
*A61K 31/505* (2006.01)
*C07D 239/02* (2006.01)

(52) U.S. Cl.
USPC ...................................................... 514/269

(58) Field of Classification Search
USPC ................................. 514/269, 275; 544/323
See application file for complete search history.

(56) References Cited

U.S. PATENT DOCUMENTS

2007/0232632 A1   10/2007   Lucking et al.
2008/0058358 A1   3/2008    Luecking et al.
2010/0076000 A1   3/2010    Lucking et al.
2011/0251222 A1*  10/2011   Lucking et al. ............. 514/275

FOREIGN PATENT DOCUMENTS

WO   2005/037800 A1   4/2005
WO   2007/071455 A1   6/2007
WO   2007/140957 A1   12/2007

OTHER PUBLICATIONS

Truce et al., Sulfones and Sulfoximines; Organic Chemistry of Sulfur, 1977, pp. 527-602.*
Verma, S, et al., "Substituted aminobenzimidazole pyrimidines as cyclin-dependent kinase inhibitors," Bioorganic & Medicinal Chemistry Letters, vol. 15, No. 8, Apr. 15, 2005, pp. 1973-1977, Elsevier Science, GB.
International Search Report, dated Jan. 19, 2010, issued in corresponding PCT/EP2009/007247.

* cited by examiner

*Primary Examiner* — James O Wilson
*Assistant Examiner* — Ebenezer O Sackey

(57) ABSTRACT

The invention relates to sulfoximine-substituted anilino-pyrimidine derivatives of formula (I).

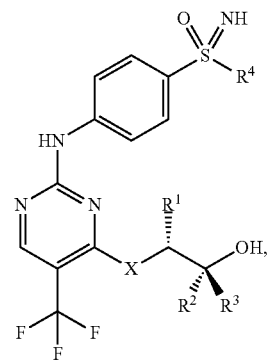

methods of production thereof, and use thereof as medication for the treatment of various diseases.

19 Claims, 8 Drawing Sheets

SULFOXIMINE-SUBSTITUTED ANILINOPYRIMIDINE DERIVATIVES AS CDK INHIBITORS, THE PRODUCTION THEREOF, AND USE AS MEDICINE

The present invention relates to selected sulfoximine-substituted anilino-pyrimidine derivatives, methods of production thereof and use thereof as medication for the treatment of various diseases.

The cyclin-dependent kinases (CDKs) are a family of enzymes that play an important role in the regulation of the cell cycle and therefore represent an especially interesting target for the development of small inhibitory molecules. Selective inhibitors of the CDKs can be used for the treatment of cancer or other diseases caused by disturbances of cellular proliferation.

Pyrimidines and analogs have already been described as active substances, for example the 2-anilino-pyrimidines as fungicides (DE 4029650) or substituted pyrimidine derivatives for the treatment of neurological or neurodegenerative diseases (WO 99/19305). Extremely varied pyrimidine derivatives have been described as CDK inhibitors, for example 2-amino-4-substituted pyrimidines (WO 01/14375), purines (WO 99/02162), 5-cyano-pyrimidines (WO 02/04429), anilinopyrimidines (WO 00/12486) and 2-hydroxy-3-N,N-dimethylaminopropoxy-pyrimidines (WO 00/39101).

In particular, pyrimidine derivatives were disclosed in WO 02/096888 and WO 03/076437 that have inhibitory effects with respect to CDKs. Compounds that contain a phenylsulfonamide group are known inhibitors of human carboanhydrases (especially carboanhydrase-2) and are used as diuretics inter alia for the treatment of glaucoma. The nitrogen atom and the oxygen atoms of the sulfonamide bind via hydrogen bridges to the zinc$^{2+}$ ion and the amino acid Thr 199 in the active center of carboanhydrase-2 and therefore block its enzymatic function (A. Casini, F. Abbate, A. Scozzafava, C. T. Supuran, Bioorganic. Med. Chem. Lett. 2003, 1, 2759). The clinical use of CDK inhibitors containing a phenylsulfonamide group might be restricted by the possibility of inhibition of the carboanhydrases and a resultant spectrum of side effects.

Examples of sulphoximine active substances are sulfonimidoyl-modified triazoles as fungicides (H. Kawanishi, H. Morimoto, T. Nakano, T. Watanabe, K. Oda, K. Tsujihara, Heterocycles 1998, 49, 181) or aralkylsulfoximines as herbicides and pesticides (Shell International Research, Ger. P. 2 129 678).

WO 2005/037800 discloses open sulfoximine-substituted anilino-pyrimidine derivatives as inhibitors of the cyclin-dependent kinases. Examples given are structures that are either unsubstituted, or substituted with halogen, in particular with bromine in the 5-position of the pyrimidine. None of the specifically disclosed structures has a 5-trifluoromethyl substituent.

Starting from this prior art, the problem faced by the present invention is to provide compounds that are not only potent CDK inhibitors, but can also effectively inhibit tumor growth. In fact, potent CDK inhibition is a necessary, but not sufficient requirement for effective tumor inhibition. The structures also require other properties, for example properties of penetration into the tumor cell.

Now it was found that compounds of general formula (I)

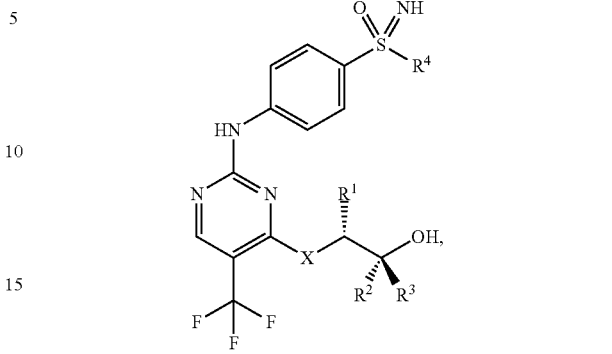

in which
X stands for —O— or —NH—, and
$R^1$ stands for a methyl, ethyl, propyl or isopropyl group, and
$R^2$ and $R^3$ stand, independently of one another, for hydrogen, a methyl or ethyl group, and
$R^4$ stands for a $C_1$-$C_6$-alkyl group or a $C_3$-$C_7$-cycloalkyl ring, and salts, diastereomers and enantiomers thereof, not only potently inhibit CDKs, but also inhibit tumor growth especially effectively.

Compounds in which X stands for —O— are grouped together with formula (Ia).

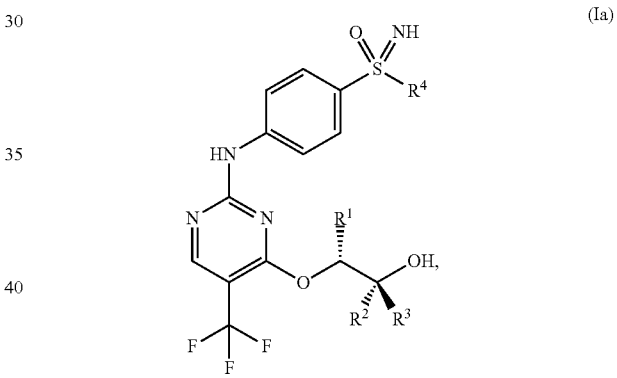

Compounds in which X stands for —NH— are grouped together with formula (Ib).

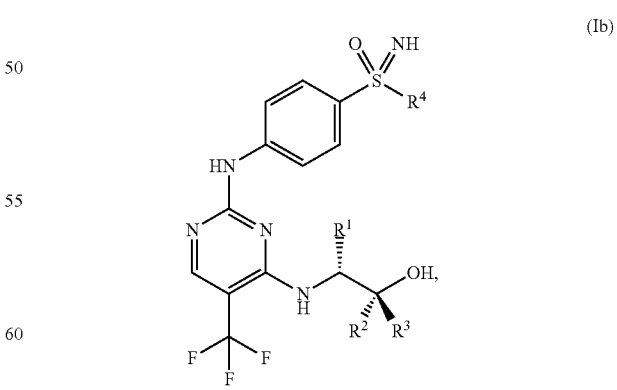

The application is based on the following definitions:
$C_1$-$C_6$-alkyl
A $C_1$-$C_6$-alkyl group is to be understood in each case as a linear or branched alkyl residue, for example a methyl, ethyl, propyl, isopropyl, butyl, isobutyl, sec. butyl, tert. butyl, pentyl, isopentyl or a hexyl residue.

$C_3$-$C_7$-cycloalkyl

A $C_3$-$C_7$-cycloalkyl ring is to be understood as a cyclopropyl, cyclobutyl, cyclopentyl, cyclohexyl or a cycloheptyl ring.

In general formula (I) X can stand for —O— or —NH—. Preferably X stands for —O—.

In general formula (I) $R^1$ can stand for a methyl, ethyl, propyl or isopropyl group.

Preferably $R^1$ stands for a methyl group.

In general formula (I), $R^2$ and $R^3$, independently of one another, can stand for hydrogen, a methyl or ethyl group.

Preferably $R^2$ and $R^3$ stand, independently of one another, for hydrogen or a methyl group.

Especially preferably $R^2$ stands for a methyl group and $R^3$ for hydrogen or a methyl group.

In general formula (I) $R^4$ can stand for a $C_1$-$C_6$-alkyl residue or a $C_3$-$C_7$-cycloalkyl ring.

Preferably $R^4$ stands for a methyl or ethyl group or for a cyclopropyl ring.

A preferred subgroup of the compounds according to general formula (I) comprises compounds according to general formula (I),
in which
X stands for —O— or —NH—, and
$R^1$ stands for a methyl group, and
$R^2$ stands for a methyl group, and
$R^3$ stands for hydrogen or a methyl group, and
$R^4$ stands for a methyl or ethyl group or for a cyclopropyl ring, and salts, diastereomers and enantiomers thereof.

The compounds according to the invention are suitable for the treatment
- of cancer, such as solid tumors, tumor metastases, and hematologic tumors, in particular:
    - head and neck tumors; lung and bronchial tumors; gastrointestinal tumors e.g. gastric carcinoma, colorectal carcinoma, pancreatic carcinoma, hepatocellular carcinoma; endokin active tumors; breast cancers and gynecological tumors; urogenital tumors, e.g. carcinoma of the kidney, urinary bladder carcinoma, prostate cancer; skin tumors; sarcomas; leukemias and lymphomas.
- of viral diseases, and
- of cardiovascular diseases such as stenoses, arterioscleroses and restenoses, stent-induced restenoses.

Formulation of the compounds according to the invention to pharmaceutical preparations is carried out in a manner known per se, by transforming the active substance or substances with the usual excipients used for galenicals to the desired dosage form.

Carriers, fillers, disintegrants, binders, humectants, glidants, absorbents and adsorbents, diluents, solvents, cosolvents, emulsifiers, solubilizers, correctives, colorants, preservatives, stabilizers, wetting agents, salts for modifying osmotic pressure or buffers can be used for example as excipients.

Reference should be made to Remington's Pharmaceutical Science, 15th ed. Mack Publishing Company, East Pennsylvania (1980).

The pharmaceutical formulations can be
in solid form, for example as tablets, sugar-coated tablets, pills, suppositories, capsules, transdermal systems or
in semi-solid form, for example as ointments, creams, gels, suppositories, emulsions or
in liquid form, for example as solutions, tinctures, suspensions or emulsions.

Excipients in the sense of the invention can for example be salts, saccharides (mono-, di-, tri-, oligo-, and/or polysaccharides), proteins, amino acids, peptides, fats, waxes, oils, hydrocarbons and derivatives thereof, wherein the excipients can be of natural origin or can be obtained synthetically or partially synthetically.

Tablets, sugar-coated tablets, capsules, pills, powders, granules, pastilles, suspensions, emulsions or solutions may in particular be considered for oral or peroral application.

Suspensions, emulsions and, above all, solutions may in particular be considered for parenteral application.

Preparation of the Compounds According to the Invention

Sulfoximines as a rule possess high stability with respect to structure and configuration (C. Bolm, J. P. Hildebrand, J. Org. Chem. 2000, 65, 169). These properties of the functional group often allow even drastic reaction conditions and make simple derivatization of the sulfoximines possible on the imine nitrogen and the α-carbon. Enantiomerically pure sulfoximines are also used as auxiliaries in diastereoselective synthesis ((a) S. G. Pyne, Sulfur Reports 1992, 12, 57; (b) C. R. Johnson, Aldrichimica Acta 1985, 18, 3).

The preparation of enantiomerically pure sulfoximines for example via resolution of the racemate with enantiomerically pure camphor-10-sulfonic acid has been described ((a) C. R. Johnson, C. W. Schroeck, J. Am. Chem. Soc. 1973, 95, 7418; (b) C. S. Shiner, A. H. Berks, J. Org. Chem. 1988, 53, 5542). Another method of preparation of optically active sulfoximines is the stereoselective imination of optically active sulfoxides ((a) C. Bolm, P. Muller, K. Harms, Acta Chem. Scand. 1996, 50, 305; (b) Y. Tamura, J. Minamikawa, K. Sumoto, S. Fujii, M. Ikeda, J. Org. Chem. 1973, 38, 1239; (c) H. Okamura, C. Bolm, Org. Lett. 2004, 6, 1305).

For review articles on sulfoximines see e.g.: a) M. Regglin, C. Zur, Synthesis 2000, 1; (b) C. R. Johnson, Aldrichimica Acta 1985, 18, 3).

The following examples explain the preparation of the compounds according to the invention, without limiting the scope of the claimed compounds to these examples.

Preparation of the Compounds of Formula (Ia) (4-O Derivatives)

The compounds according to the invention can be prepared by a method that is characterized by the following steps:

a) Oxidation of a compound of formula (IVd) to the sulfoxide of formula (IVc).

(IVd)

(IVc)

b₁) Direct imination of the sulfoxide of formula (IVc) to a protected sulfoximine of formula (IVa).

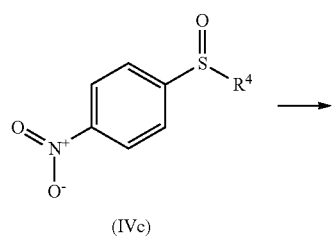

or
b₂) Imination of the sulfoxide of formula (IVc) to an unprotected sulfoximine of formula (IVb) and subsequent introduction of the protective group to a compound of formula (IVa).

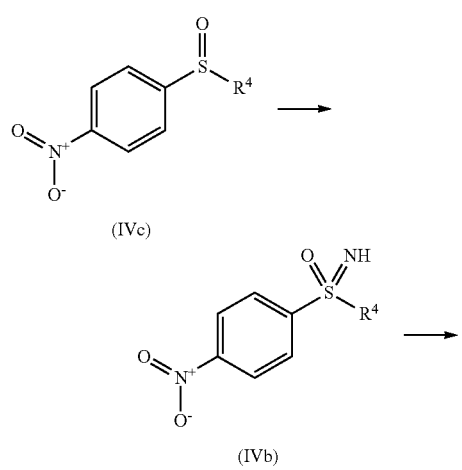

c) Reduction of the compound of formula (IVa) to a compound of formula (IV)

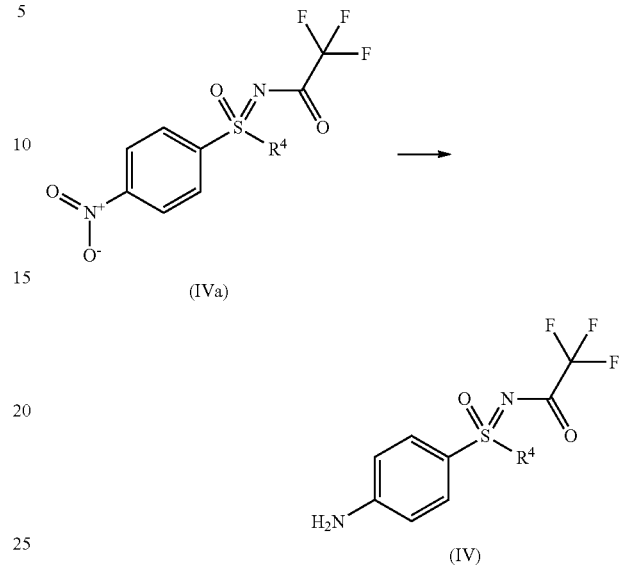

d) Functionalization of the 4-position of 2,4-dichloro-5-iodo-pyrimidine (VII) by reaction with a mono-protected diol of formula (VI) with formation of an intermediate of formula (Va).

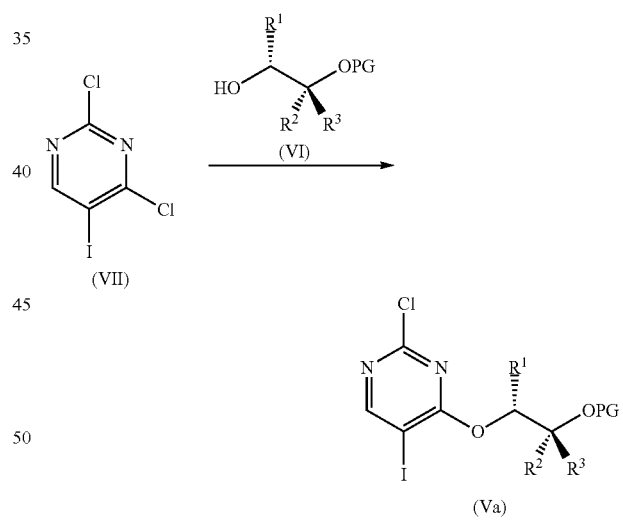

e) Preparation of the 5-CF₃ intermediate (V).

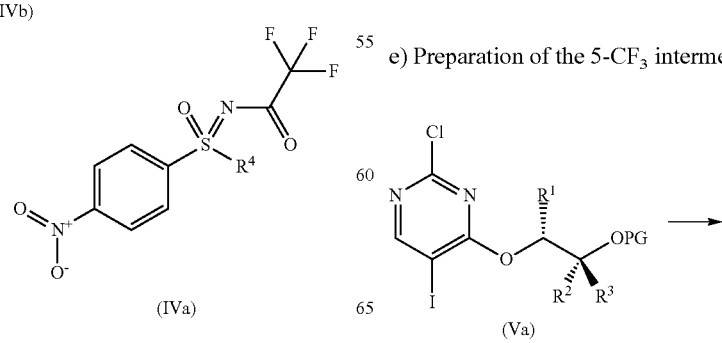

g) Cleavage of the protective group (PG) with formation of (II).
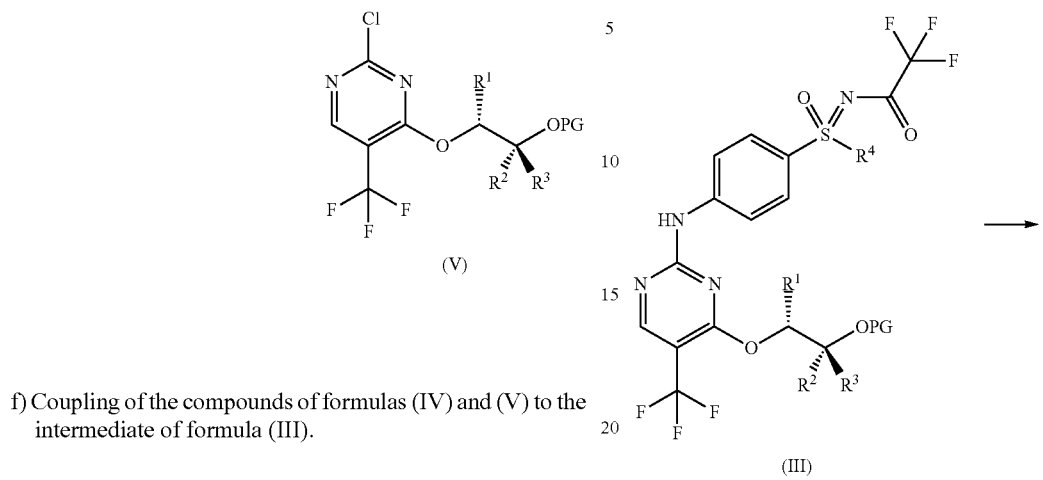
f) Coupling of the compounds of formulas (IV) and (V) to the intermediate of formula (III).
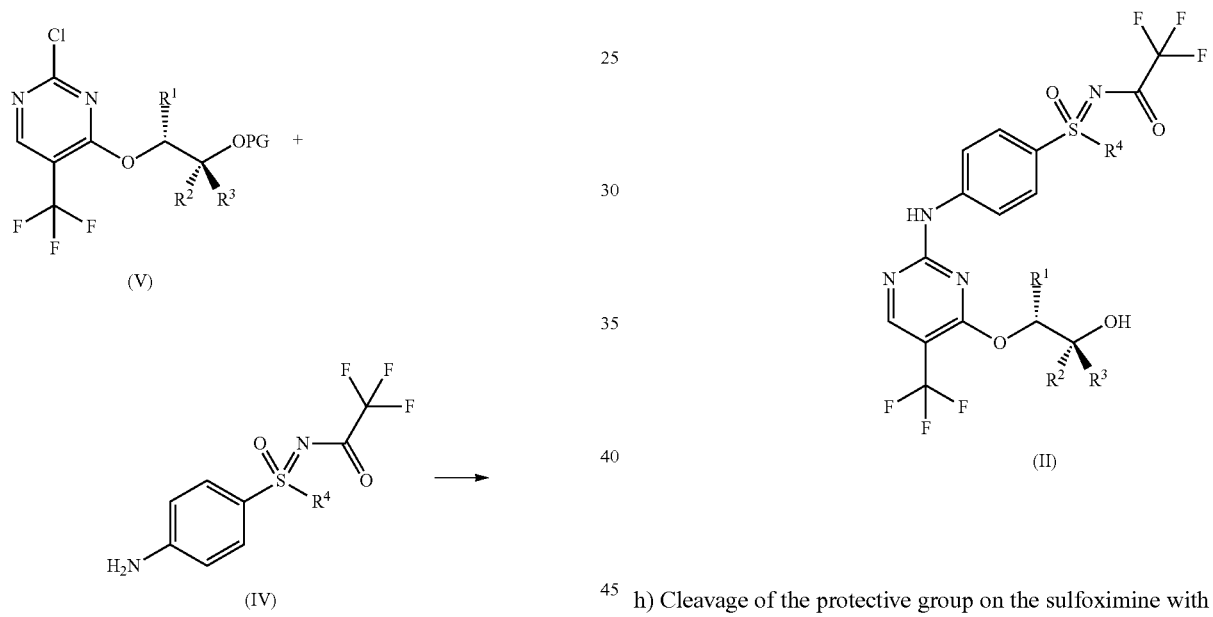
h) Cleavage of the protective group on the sulfoximine with formation of (Ia).
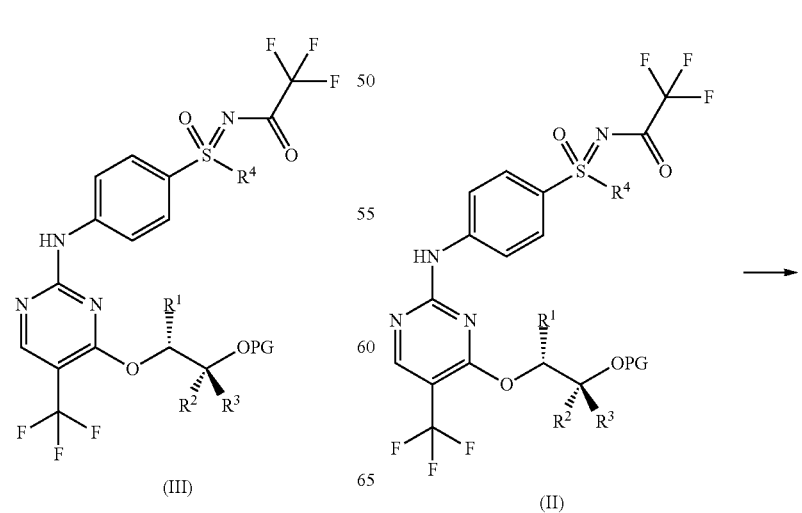

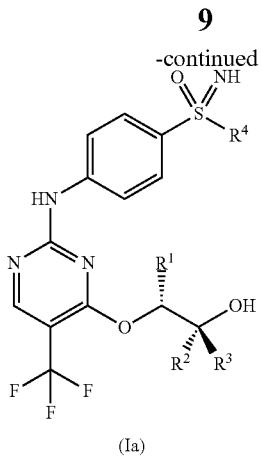

(Ia)

where the substituents R¹, R², R³ and R⁴ have the meanings stated in general formula (I).

Step a)

A compound of formula (IVd) is oxidized to the sulfoxide of formula (IVc). Numerous methods, including stereoselective methods, are available for transforming a thioether to a sulfoxide (see e.g.: (a) M. N. Ali et al., Synthesis 1997, 764; b) M. C. Carreno, Chem. Rev. 1995, 95, 1717; c) I. Patel et al., Org. Proc. Res. Dev. 2002, 6, 225; c) N. Khiar et al., Chem. Rev. 2003, 103, 3651). The described use of periodic acid/iron(III) chloride is especially suitable for the preparation of compounds of formula (IVc).

Step b₁)

The reaction of a sulfoxide of formula (IVc) with trifluoroacetamide in combination with iodobenzene diacetate, magnesium oxide and catalytic amounts of rhodium(II) acetate dimer makes possible the preparation of a protected sulfoximine of formula (IVa). This reaction is stereospecific and takes place with retention of the configuration at the stereocenter (see: (a) H. Okamura, C. Bolm, Org. Lett. 2004, 6, 1305).

Step b₂)

First there is reaction of a sulfoxide of formula (IVc) to an unprotected sulfoximine of formula (IVb). Suitable methods are for example:

a) Reaction of the sulfoxide with sodium azide/conc. sulfuric acid (see e.g.: (a) C. R. Johnson, P. E. Rogers, J. Org. Chem. 1973, 38, 1793).

b) Reaction of the sulfoxide with sodium azide/oleum (see e.g.: (a) N. V. Kondratenko, O. A. Radchenko, L. M. Yagupol'ski, J. Org. Chem. USSR 1984, 20, 2051).

c) Reaction of the sulfoxide with o-mesitylene sulfonylhydroxylamine (MSH) (see e.g.: (a) C. R. Johnson, R. A. Kirchhoff, H. G. Corkins, J. Org. Chem. 1974, 39, 2458). The subsequent introduction of the protective group with formation of compounds of formula (IVa) can for example take place as described by reaction with trifluoroacetic anhydride in basic conditions.

Step c)

For the subsequent reduction of the aromatic nitro group to a compound of formula (IV), in principle a number of reaction conditions are available (see e.g.: R. C. Larock, *Comprehensive Organic Transformations*, VCH, New York, 1989, 411). The described use of titanium(III) chloride or hydrogenation using palladium on charcoal, for example, is especially suitable.

Step d)

Reaction of 2,4-dichloro-5-iodo-pyrimidine (VII) with an alcohol of formula (VI) makes possible the preparation of an intermediate of formula (Va) (see e.g.: U. Lücking et al., WO2007/071455).

Step e)

In principle, various methods are available for the replacement of a halogen with a trifluoromethyl group in a nitrogen-containing heteroaromatic (see e.g.: a) G. E. Carr, R. D. Chambers, T. F. Holmes, J. Chem. Soc. Perkin Trans. 1, 1988, 921; b) F. Cottet, M. Schlosser, Eur. J. Org. Chem. 2002, 327; c) F. G. Njoroge et al., J. Med. Chem 1997, 40, 4290).

In particular the described use of copper(I) iodide, potassium fluoride and (trifluoromethyl)-trimethylsilane in N-methyl-2-pyrrolidinone and THF is suitable for the introduction of the pyrimidine (Va) in the 5-position with formation of intermediate (V).

Step f)

A 2-chloro-pyrimidine of formula (V) can be reacted with an aniline of formula (IV) to an intermediate of formula (III) (see e.g.: (a) J. Bryant et al., WO 2004/048343).

Step g)

Cleavage of the protective group (PG) from intermediate (III) yields intermediate (II) (see e.g.: P. J. Kocienski, Protecting Groups, Georg Thieme Verlag Stuttgart, New York, 1994).

The hydrogenation described is especially suitable for the described cleavage of a benzyl group. The cleavage of a THP group can if necessary already take place in the conditions of step f).

Step h)

Cleavage of the trifluoroaceto group on the sulfoximine (II) gives the compound of formula (Ia). The technique described, using potassium carbonate in methanol at room temperature, is especially suitable for this (see e.g.: (a) H. Okamura, C. Bolm, Org. Lett. 2004, 6, 1305).

General Information

All reactions with oxidation-sensitive or hydrolysis-sensitive compounds were carried out under argon, with dried solvents.

With the exception of the sulfoximine derivatives, the substances were named using the program *Autonom* 2000 *Name*, which is implemented in MDL ISIS Draw. *Autonom* 2000 *Name* does not accept any sulfoximines, therefore the sulfoximines were named following IUPAC rules (IUPAC, Nomenclature of Organic Chemistry, 1979 Edition, C-6.3. Sulfoxides and Sulfones, Rule C-633, 633.1 Sulfimide and Sulfoximide).

Abbreviations

| Abbreviation | Meaning |
|---|---|
| Ac | Acetyl |
| Aloc | Allyloxycarbonyl |
| Boc | tert-Butyloxycarbonyl |
| BOM | Benzyloxymethyl |
| br | Broad |
| CI | Chemical ionization |
| d | Doublet |
| dd | Doublet of doublet |
| DCM | Dichloromethane |
| DMF | N,N-Dimethylformamide |
| DMSO | Dimethylsulfoxide |
| ESI | Electrospray ionization |
| HPLC | High performance liquid chromatography |
| m | Multiplet |
| MEM | (2-Methoxyethoxy)methyl |
| MOM | Methoxymethyl |
| MS | Mass spectrometry |
| MTM | Methylthiomethyl |
| NMP | N-Methyl-2-pyrrolidinone |
| NMR | Nuclear magnetic resonance spectroscopy: chemical shift (δ) is given in ppm. |

| Abbreviation | Meaning |
|---|---|
| Pg | Protective group comprising groups such as TMS, TES, TBDMS, TBDPS, TIPS, Benzyl, PMB, Trityl, Allyl, Aloc, MOM, MTM, MEM, BOM, SEM, THP. |
| PMB | p-Methoxybenzyl |
| q | Quartet |
| s | Singlet |
| SEM | β-(Trimethylsilypethoxymethyl |
| TBDMS | tert.-Butylsilyldimethyl |
| TBDPS | tert.-Butylsilyldiphenyl |
| TEA | Triethylamine |
| TES | Triethylsilyl |
| THF | Tetrahydrofuran |
| THP | Tetrahydropyranyl |
| TIPS | Triisopropyl |
| TMS | Trimethylsilyl |
| tr | Triplet |

EXAMPLE 1

(RS)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide

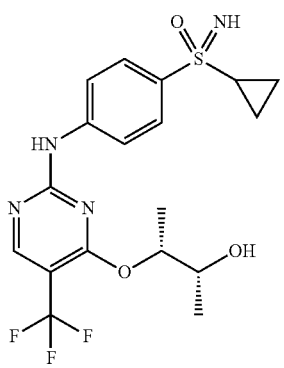 [SMILES: C[C@@H](O)[C@@H](C)Oc1nc(Nc2ccc(S(=N)(=O)C3CC3)cc2)ncc1C(F)(F)F]

1a) Preparation of the Intermediates

Compound 1.1

1-Cyclopropylsulfanyl-4-nitrobenzene

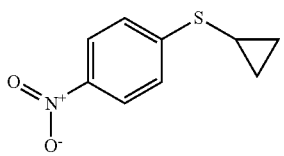 [SMILES: O=[N+]([O-])c1ccc(SC2CC2)cc1]

1.78 g (44.6 mmol) of sodium hydride (60%) was added in portions to a solution of 3.00 g (40.5 mmol) of cyclopropane thiol (preparation according to: E. Block et al., *J. Am. Chem. Soc.* 1992, 114, 3492) in 100 ml THF/100 ml diethyl ether and was stirred for 30 minutes at room temperature. Then 6.00 g (38.7 mmol) of 1-fluoro-4-nitrobenzene was added in portions. The mixture was stirred for 2 hours at 40° C. After it had cooled, the mixture was put in water and was extracted with benzene (3×). The combined organic phases were concentrated by evaporation and the residue was purified chromatographically (hexane/ethyl acetate 95:5). 4.6 g (23.6 mmol; yield: 61%) of the product was obtained.

$^1$H-NMR (400 MHz, DMSO): δ=8.12 (m, 2H), 7.54 (m, 2H), 2.35 (m, 1H), 1.16 (m, 2H), 0.61 (m, 2H).

Compound 1.2

(RS)-1-Cyclopropane sulfinyl-4-nitrobenzene

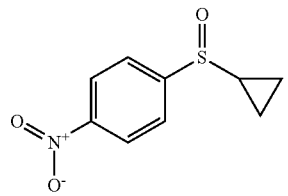 [SMILES: O=[N+]([O-])c1ccc(S(=O)C2CC2)cc1]

179 mg (1.11 mmol) of iron(III) chloride was added to a mixture of 7.2 g (36.88 mmol) of 1-cyclopropylsulfanyl-4-nitrobenzene in 140 ml acetonitrile and it was stirred for 15 minutes at room temperature. Then 9.25 g (40.57 mmol) of periodic acid was added in portions at 25° C. The mixture was stirred for 30 minutes and then added, while stirring, to a cooled saturated sodium thiosulfate solution. It was then extracted with ethyl acetate (2×). The combined organic phases were dried (Na$_2$SO$_4$), filtered and concentrated by evaporation. The residue obtained was purified chromatographically (hexane/ethyl acetate 1:1). 5.93 g (28.07 mmol; yield: 76%) of the product was obtained.

$^1$H-NMR (400 MHz, DMSO):δ=8.41 (m, 2H), 7.98 (m, 2H), 2.60 (m, 1H), 1.01 (m, 3H), 0.86 (m, 1H).

Compound 1.3

(RS)-S-Cyclopropyl-S-(4-nitrophenyl)-N-(trifluoroacetyl)sulfoximide

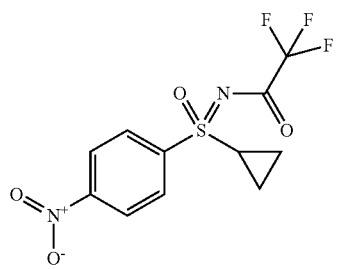 [SMILES: O=C(N=S(=O)(c1ccc([N+](=O)[O-])cc1)C1CC1)C(F)(F)F]

1.58 g (3.58 mmol) of rhodium(II) acetate dimer was added, under argon, to a suspension of 15.1 g (71.53 mmol) (RS)-1-cyclopropane sulfinyl-4-nitrobenzene, 17.8 g (157.37 mmol) trifluoroacetamide, 38.0 g (118.02 mmol) iodobenzene diacetate and 12.7 g (314.73 mmol) magnesium oxide in 801 ml DCM and stirred overnight at room temperature. The mixture was filtered through Celite with suction and concentrated by evaporation. The residue that remained was purified chromatographically (hexane/ethyl acetate 2:1). 18.0 g (55.97 mmol; yield: 78%) of the product was obtained.

¹H-NMR (400 MHz, DMSO): δ=8.49 (m, 2H), 8.25 (m, 2H), 3.56 (m, 1H), 1.51 (m, 1H), 1.41 (m, 1H), 1.18 (m, 2H).

Compound 1.4

(RS)-S-(4-Aminophenyl)-S-cyclopropyl-N-(trifluoroacetyl)sulfoximide

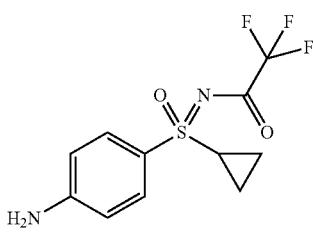 [SMILES: Nc1ccc(S(=O)(=NC(=O)C(F)(F)F)C2CC2)cc1]

1.4 g palladium on charcoal (10%/50% moisture) was added to a solution of 6.9 g (21.44 mmol) (RS)-S-cyclopropyl-S-(4-nitrophenyl)-N-(trifluoroacetyl)sulfoximide in 214 ml ethanol and 39 ml THF and was hydrogenated for 1 hour under normal pressure at 25° C. A further 1.4 g palladium on charcoal was added, and it was hydrogenated for a further 4.5 hours at normal pressure. The mixture was filtered, 1.4 g palladium on charcoal was added to the filtrate again and finally hydrogenated for 45 minutes. The mixture was filtered and concentrated by evaporation. 5.8 g (19.91 mmol; yield: 93%) of the product was obtained.

¹H-NMR (400 MHz, DMSO): δ=7.53 (m, 2H), 6.71 (m, 2H), 6.40 (br, 2H), 3.21 (m, 1H), 1.28 (m, 2H), 1.08 (m, 2H).

Compound 1.5

(2R,3R)-3-Benzyloxy-butan-2-ol

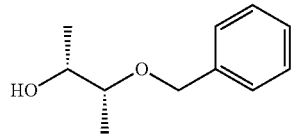

5.00 g (44.6 mmol) of potassium tert.-butylate was added to a solution of 4.00 g (44.4 mmol) (2R,3R)-butane-2,3-diol in 300 ml THF at room temperature and the mixture was refluxed for 15 minutes. The mixture was cooled to approx. 50° C. and 5.3 ml (44.6 mmol) benzyl bromide was added. It was refluxed for 3 hours, and was then stirred overnight at room temperature. The mixture was diluted with ethyl acetate and sodium chloride solution and then washed with 1N hydrogen chloride solution (1×) and sodium chloride solution (2×). The organic phase was dried (Na₂SO₄), filtered and concentrated by evaporation. The residue obtained was purified chromatographically (hexane/ethyl acetate 1:1). 3.41 g (18.9 mmol; yield: 43%) of the product was obtained.

¹H-NMR (400 MHz, DMSO): δ=7.35 (m, 4H), 7.28 (m, 1H), 4.52 (m, 3H), 3.67 (m, 1H), 3.37 (m, 1H), 1.05 (d, 3H), 1.01 (d, 3H).

Compound 1.6

4-((1R,2R)-2-Benzyloxy-1-methyl-propoxy)-2-chloro-5-iodo-pyrimidine

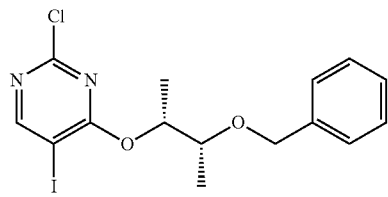 [SMILES: C[C@@H](OCc1ccccc1)[C@@H](C)Oc1nc(Cl)ncc1I]

2.07 g sodium hydride (55%) was added in portions to 8.55 g (47.4 mmol) (2R,3R)-3-benzyloxy-butan-2-ol in 56 ml diethyl ether at 0° C. with stirring. After 10 minutes the ice bath was removed and it was stirred for a further 3 minutes at room temperature. The suspension formed was added at 0° C. to a solution of 6.52 g (23.7 mmol) of 2,4-dichloro-5-iodo-pyrimidine. The mixture was stirred for 4 hours at 40° C. and then dilute sodium chloride solution was added. It was then extracted with ethyl acetate (2×). The combined organic phases were dried (Na₂SO₄), filtered and concentrated by evaporation. The residue obtained was chromatographically (hexane/ethyl acetate 4:1). 4.12 g (9.8 mmol; yield: 41%) of the product was obtained.

¹H-NMR (400 MHz, DMSO): δ=8.78 (s, 1H), 7.29 (m, 5H), 5.27 (m, 1H), 4.64 (d, 1H), 4.53 (d, 1H), 3.73 (m, 1H), 1.30 (d, 3H), 1.19 (d, 3H).

Compound 1.7

4-((1R,2R)-2-Benzyloxy-1-methyl-propoxy)-2-chloro-5-trifluoromethyl-pyrimidine

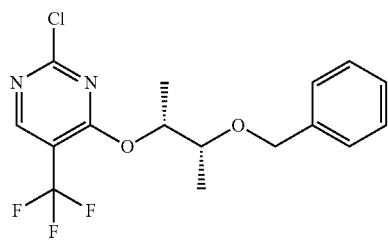 [SMILES: C[C@@H](OCc1ccccc1)[C@@H](C)Oc1nc(Cl)ncc1C(F)(F)F]

3.82 g (20.0 mmol) of copper(I) iodide, 0.97 g (16.7 mmol) of potassium fluoride and 2.47 ml (16.7 mmol) (trifluoromethyl)-trimethylsilane were added, with stirring, to a solution of 4.66 g (11.1 mmol) of 4-((1R,2R)-2-benzyloxy-1-methyl-propoxy)-2-chloro-5-iodo-pyrimidine in 15.8 ml NMP and 15.8 ml THF at room temperature. The mixture was stirred for 5.5 hours at 80° C. After cooling, the mixture was added to dilute sodium chloride solution and was extracted with ethyl acetate (2×). The combined organic phases were dried (Na₂SO₄), filtered and concentrated by evaporation. The residue obtained was chromatographically (hexane/ethyl acetate 4:1). 2.17 g (6.0 mmol; yield: 54%) of the product was obtained.

¹H-NMR (400 MHz, DMSO): δ=8.81 (s, 1H), 7.21 (m, 5H), 5.40 (m, 1H), 4.57 (d, 1H), 4.42 (d, 1H), 3.70 (m, 1H), 1.28 (d, 3H), 1.13 (d, 3H).

Compound 1.8

(RS)-S-(4-{[4-{[(1R,2R)-2-(Benzyloxy)-1-methyl-propyl]oxy}-5-(trifluoromethyl)pyrimidin-2-yl]amino}phenyl)-S-cyclopropyl-N-(trifluoroacetyl)sulfoximide

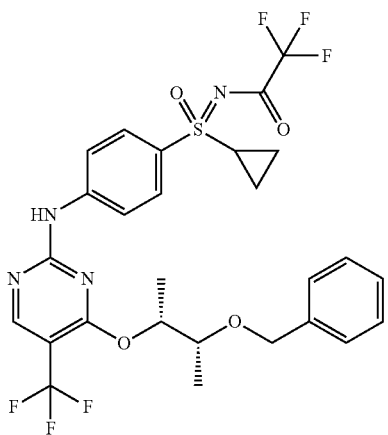 [SMILES: C[C@@H](OCc1ccccc1)[C@@H](C)Oc1nc(Nc2ccc(S(=O)(=NC(=O)C(F)(F)F)C3CC3)cc2)ncc1C(F)(F)F]

0.96 ml of 4N solution of hydrogen chloride in dioxane was added to 1.39 g (3.85 mmol) of 4-((1R,2R)-2-benzyloxy-1-methyl-propoxy)-2-chloro-5-trifluoromethyl-pyrimidine and 1.35 g (4.62 mmol) (RS)-S-(4-aminophenyl)-S-cyclopropyl-N-(trifluoroacetyl)sulfoximide in 18.8 ml acetonitrile and stirred for 5 hours at 80° C. After cooling, the mixture was diluted with ethyl acetate and washed with saturated sodium hydrogencarbonate solution and saturated sodium chloride solution, dried (Na₂SO₄), filtered and concentrated by evaporation. The residue obtained was purified chromatographically (hexane/ethyl acetate 4:1). 1.32 g (2.14 mmol, yield: 56%) of the product was obtained.

¹H-NMR (400 MHz, DMSO): δ=10.71 (s, 1H), 8.84 (s, 1H), 8.08 (m, 2H), 7.93 (m, 2H), 7.26 (m, 5H), 5.52 (m, 1H), 4.62 (d, 1H), 4.51 (d, 1H), 3.78 (m, 1H), 3.35 (m, 1H), 1.37 (m, 5H), 1.16 (m, 5H).

Compound 1.9

(RS)-S-Cyclopropyl-S-(4-{[4-{[(1R,2R)-2-hydroxy-1-methylpropyl]oxy}-5-(trifluoromethyl)pyrimidin-2-yl]amino}phenyl)-N-(trifluoroacetyl)sulfoximide

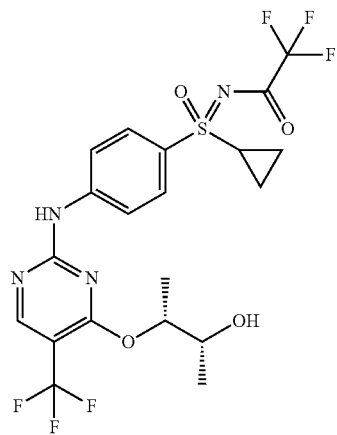 [SMILES: C[C@@H](O)[C@@H](C)Oc1nc(Nc2ccc(S(=O)(=NC(=O)C(F)(F)F)C3CC3)cc2)ncc1C(F)(F)F]

1.64 g palladium on charcoal (10%) was added to a solution of 1.31 g (2.12 mmol) (RS)-S-(4-{([4-{[(1R,2R)-2-(benzyloxy)-1-methylpropyl]oxy}-5-(trifluoromethyl)pyrimidin-2-yl]amino}phenyl)-S-cyclopropyl-N-(trifluoroacetyl)sulfoximide in 66 ml ethanol and was hydrogenated at normal pressure at room temperature. The mixture was filtered and concentrated by evaporation. 0.88 g (1.67 mmol; yield: 79%) of the product was obtained.

¹H-NMR (400 MHz, DMSO): δ=10.65 (s, 1H), 8.58 (s, 1H), 8.04 (m, 2H), 7.89 (m, 2H), 5.28 (m, 1H), 4.86 (d, 1H), 3.82 (m, 1H), 3.35 (m, 1H), 1.45 (m, 5H), 1.15 (m, 5H).

1b) Preparation of the End Product 1130 mg (8.20 mmol) of potassium carbonate was added to 863 mg (1.64 mmol) (RS)-S-cyclopropyl-S-(4-{([4-{[(1R,2R)-2-hydroxy-1-methylpropyl]oxy}-5-(trifluoromethyl)pyrimidin-2-yl]amino}phenyl)-N-(trifluoroacetyl)sulfoximide in 35 ml methanol and was stirred for 1.5 hours at room temperature. It was diluted with saturated sodium chloride solution and was extracted with ethyl acetate (3×). The combined organic phases were dried (Na₂SO₄), filtered and concentrated by evaporation. 709 mg (1.64 mmol) of the raw product was obtained.

¹H-NMR (400 MHz, DMSO): δ=10.50 (s, 1H), 8.59 (s, 1H), 7.94 (m, 2H), 7.84 (m, 2H), 5.32 (m, 1H), 4.91 (d, 1H), 4.07 (s, 1H), 3.86 (m, 1H), 2.63 (m, 1H), 1.30 (d, 3H), 1.11 (m, 4H), 0.91 (m, 3H).

MS: 431 (ES+).

The mixture of diastereomers was separated into the pure stereoisomers by preparative HPLC:

Column: Chiralpak IA 5μ 250×30 mm

Eluents: Hexane/ethanol 8:2

Flow: 40.0 mL/min

Detector: UV 254 nm

Temperature: Room temperature

Retention time: 10.8-13.4 min; stereoisomer 1 (=example 1-SI-1)

13.6-18.5 min; stereoisomer 2 (=example 1-SI-2)

EXAMPLE 2

(RS)-S-(4-{[4-{[(1R,2R)-2-Hydroxy-1-methylpropyl]oxy}-5-(trifluoromethyl)pyrimidin-2-yl]amino}phenyl)-S-methylsulfoximide

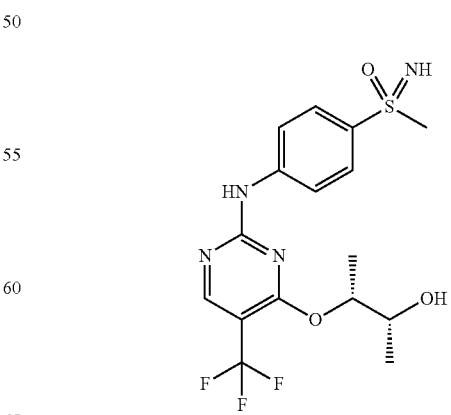

2a) Preparation of the Intermediates

Compound 2.1

(RS)-S-(4-Nitrophenyl)-S-methylsulfoximide

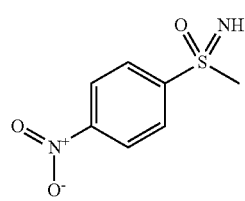

0.70 g (10.76 mmol) of sodium azide was added to 1.56 g (8.42 mmol) of 1-(methylsulfinyl)-4-nitrobenzene in 20 ml DCM. 2.3 ml concentrated sulfuric acid was slowly added to the mixture at 0° C. and it was then heated to 45° C. After 16 h the mixture was cooled to room temperature, and after adding water it was extracted with DCM. The aqueous phase was adjusted to pH 11 with 15% sodium hydroxide solution and extracted with DCM (2×). The combined organic phases were dried ($Na_2SO_4$), filtered and concentrated by evaporation. 1.08 g (5.39 mmol; yield: 63%) of the product was obtained.

$^1$H-NMR (400 MHz, DMSO): δ=8.43 (m, 2H), 8.17 (m, 2H), 4.62 (s, 1H), 3.18 (s, 3H).

Compound 2.2

(RS)-S-Methyl-S-(4-nitrophenyl)-N-(trifluoroacetyl)sulfoximide

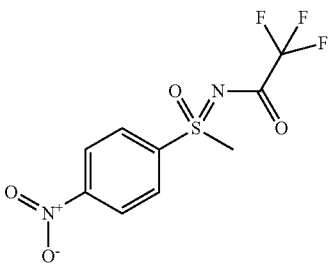 [SMILES: CS(=O)(=NC(=O)C(F)(F)F)c1ccc([N+](=O)[O-])cc1]

1.00 ml (7.08 mmol) of trifluoroacetic anhydride was added dropwise, with cooling with ice, to a solution of 1000 mg (4.99 mmol) (RS)-S-(4-nitrophenyl)-S-methylsulfoximide, 55 mg (0.45 mmol) DMAP and 0.76 ml (5.49 mmol) triethylamine in 32 ml DCM. The mixture was stirred for a further 2 hours on the ice bath. It was diluted with DCM and washed with semiconcentrated sodium chloride solution. The organic phase was dried ($Na_2SO_4$), filtered and concentrated by evaporation. The residue obtained was purified chromatographically (hexane/ethyl acetate 60:40). The product obtained was finally stirred with diisopropyl ether. The solid was filtered off with suction and dried. 1444 mg (4.87 mmol; yield: 98%) of the product was obtained.

$^1$H-NMR (400 MHz, DMSO): δ=8.50 (m, 2H), 8.24 (m, 2H), 3.87 (s, 3H).

Compound 2.3

(RS)-S-(4-Aminophenyl)-S-methyl-N-(trifluoroacetyl)sulfoximide

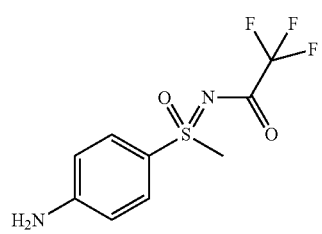 [SMILES: CS(=O)(=NC(=O)C(F)(F)F)c1ccc(N)cc1]

292 mg palladium on charcoal (10%/50% moisture) was added to a solution of 1.34 g (4.52 mmol) (RS)-S-methyl-S-(4-nitrophenyl)-N (trifluoroacetyl)sulfoximide in 45 ml ethanol and 8 ml THF and was hydrogenated for 45 minutes under normal pressure at 24° C. The mixture was filtered and concentrated by evaporation. The residue obtained was stirred with diisopropyl ether. The solid was filtered off with suction and dried. 1.07 g (4.03 mmol; yield: 89%) of the product was obtained.

$^1$H-NMR (400 MHz, DMSO): δ=7.54 (m, 2H), 6.67 (m, 2H), 6.35 (s, 2H), 3.55 (s, 3H).

Compound 2.4

(RS)-S-(4-{[4-{[(1R,2R)-2-(Benzyloxy)-1-methylpropyl]oxy}-5-(trifluoromethyl)pyrimidin-2-yl]amino}phenyl)-S-methyl-N-(trifluoroacetyl)sulfoximide

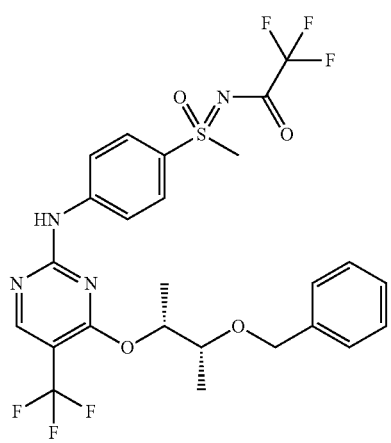 [SMILES: C[C@@H](OCc1ccccc1)[C@@H](C)Oc1nc(Nc2ccc(S(C)(=O)=NC(=O)C(F)(F)F)cc2)ncc1C(F)(F)F]

0.97 ml of 4N solution of hydrogen chloride in dioxane was added to 1.40 g (3.88 mmol) of 4-((1R,2R)-2-benzyloxy-1-methyl-propoxy)-2-chloro-5-trifluoromethyl-pyrimidine and 1.20 g (4.51 mmol) (RS)-S-(4-aminophenyl)-S-methyl-N-(trifluoroacetyl)sulfoximide in 19.0 ml acetonitrile and was then stirred for 6 hours at 80° C. After cooling, the mixture was diluted with ethyl acetate and washed with saturated sodium hydrogencarbonate solution and saturated sodium chloride solution, dried (Na$_2$SO$_4$), filtered and concentrated by evaporation. The residue is obtained was purified chromatographically (hexane/ethyl acetate 1:1). 1.76 g (2.98 mmol, yield: 77%) of the product was obtained.

$^1$H-NMR (400 MHz, DMSO): δ=10.66 (s, 1H), 8.60 (s, 1H), 8.02 (m, 2H), 7.93 (m, 2H), 7.21 (m, 5H), 5.46 (m, 1H), 4.57 (d, 1H), 4.46 (d, 1H), 3.72 (m, 1H), 3.68 (s, 3H), 1.31 (d, 3H), 1.16 (d, 3H).

Compound 2.5

(RS)-S-(4-{[4-{[(1R,2R)-2-Hydroxy-1-methylpropyl]oxy}-5-(trifluoromethyl)pyrimidin-2-yl]amino}phenyl)-S-methyl-N-(trifluoroacetyl)sulfoximide

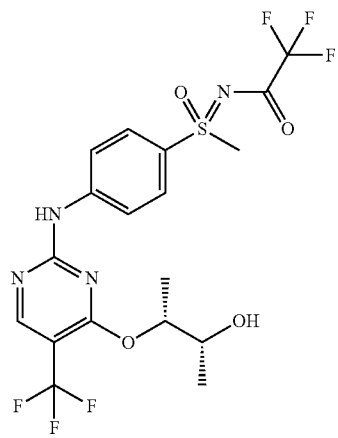 [SMILES: C[C@@H](O)[C@@H](C)Oc1nc(Nc2ccc(S(C)(=O)=NC(=O)C(F)(F)F)cc2)ncc1C(F)(F)F]

0.18 g palladium on charcoal (10%) was added to a solution of 1.75 g (2.96 mmol) of (RS)-S-(4-{[4-{[(1R,2R)-2-(benzyloxy)-1-methylpropyl]oxy}-5-(trifluoromethyl)pyrimidin-2-yl]amino}phenyl)-S-methyl-N-(trifluoroacetyl)sulfoximide in 35 ml ethanol and it was hydrogenated at normal pressure at room temperature. The mixture was filtered and concentrated by evaporation. 1.40 g of the raw product was obtained.

$^1$H-NMR (400 MHz, DMSO): δ=10.65 (s, 1H), 8.58 (s, 1H), 8.04 (m, 2H), 7.93 (m, 2H), 5.28 (m, 1H), 4.86 (d, 1H), 3.83 (m, 1H), 3.70 (s, 3H), 1.26 (d, 3H), 1.07 (d, 3H).

2b) Preparation of the End Product 1.92 g (13.89 mmol) of potassium carbonate was added to 1.39 g (2.78 mmol) (RS)-S-(4-{[4-{[(1R,2R)-2-hydroxy-1-methylpropyl]oxy}-5-(trifluoromethyl)pyrimidin-2-yl]amino}phenyl)-S-methyl-N-(trifluoroacetyl)sulfoximide in 60 ml methanol and stirred for 1.5 hours at room temperature. It was diluted with saturated sodium chloride solution and extracted with ethyl acetate (2×). The combined organic phases were dried (Na$_2$SO$_4$), filtered and concentrated by evaporation. The residue was purified chromatographically (DCM/EtOH 9:1). 862 mg (2.13 mmol; yield: 77%) of the product was obtained.

$^1$H-NMR (400 MHz, DMSO): δ=10.47 (s, 1H), 8.55 (s, 1H), 7.90 (m, 2H), 7.83 (m, 2H), 5.27 (m, 1H), 4.86 (d, 1H), 4.04 (s, 1H), 3.82 (m, 1H), 3.00 (s, 3H), 1.26 (d, 3H), 1.07 (d, 3H).

The mixture of diastereomers was separated into the pure stereoisomers by preparative HPLC:

Column: Chiralpak IC 5µ 250×20 mm

Eluents: Hexane/ethanol 8:2

Buffer: Hexane/0.1% DEA

Flow: 25.0 mL/min

Detector: UV 280 nm

Temperature: Room temperature

Retention time: 9.5-12.1 min; stereoisomer 1 (=example 2-SI-1)

13.1-16.0 min; stereoisomer 2 (=example 2-SI-2)

EXAMPLE 3

(RS)-S-(4-{[4-{[(R)-2-Hydroxy-1,2-dimethylpropyl]oxy}-5-(trifluoromethyl)pyrimidin-2-yl]amino}phenyl)-S-methylsulfoximide

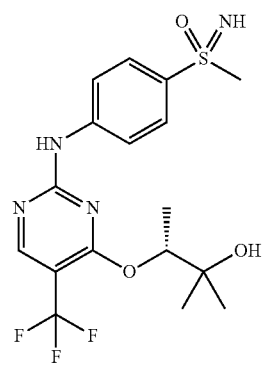 [SMILES: C[C@@H](Oc1nc(Nc2ccc(S(C)(=N)=O)cc2)ncc1C(F)(F)F)C(C)(C)O]

3a) Preparation of the Intermediates

Compound 3.1

(R)-2-Methyl-butane-2,3-diol

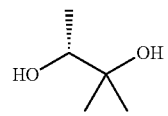

A solution of 10.0 g (96.1 mmol) (R)-(+)-methyl lactate in 20 ml THF was slowly added dropwise to 160 ml (480.0 mmol) of an ice-cooled 3N solution of methylmagnesium chloride in THF. The mixture was first heated slowly to room temperature and then refluxed for 30 minutes. After cooling, the mixture was added to a saturated ammonium chloride solution and was extracted with ethyl acetate (3×). The combined organic phases were filtered on a Whatman filter and concentrated by evaporation. 4.5 g (43.1 mmol) of the raw product was obtained, and was used without further purification.

¹H-NMR (400 MHz, DMSO): δ=4.21 (d, 1H), 3.93 (s, 1H), 3.29 (m, 1H), 0.97 (m, 9H).

Compound 3.2

(R)-3-(2-Chloro-5-iodo-pyrimidin-4-yloxy)-2-methyl-butan-2-ol

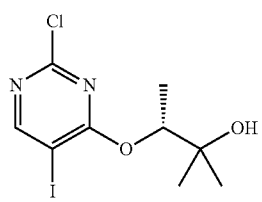

1.84 g (42.3 mmol) of sodium hydride (55%) was added in portions, with stirring at 0° C., to a solution of 4.40 g (42.3 mmol) (R)-2-methyl-butane-2,3-diol in 83 ml diethyl ether and was stirred for 10 minutes. It was stirred for a further 3 minutes at room temperature and the mixture was then added to an ice-cooled solution of 9.68 g (35.2 mmol) of 2,4-dichloro-5-iodo-pyrimidine in 97 ml acetonitrile. The mixture was stirred for 4 hours at 40° C. and, after cooling, ice and saturated NaCl solution were added. It was then extracted with ethyl acetate (3×). The combined organic phases were dried (Na₂SO₄), filtered and concentrated by evaporation. The residue obtained was purified chromatographically (hexane/ethyl acetate 4:1). 4.96 g (14.5 mmol; yield: 41%) of the product was obtained.

¹H-NMR (400 MHz, DMSO): δ=8.73 (s, 1H), 4.96 (q, 1H), 4.62 (s, 1H), 1.21 (d, 3H), 1.13 (s, 6H).

ES: 343 (Cl+).

Compound 3.3

2-Chloro-4-[(R)-1,2-dimethyl-2-(tetrahydro-pyran-2-yloxy)-propoxy]-5-iodo-pyrimidine

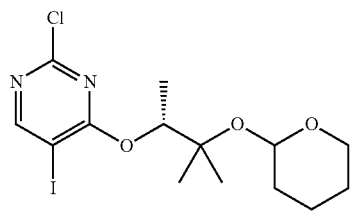 [SMILES: C[C@@H](Oc1nc(Cl)ncc1I)C(C)(C)OC1CCCCO1]

2.64 ml (29.0 mmol) dihydropyran and 0.36 g (1.5 mmol) pyridinium tosylate were added to a solution of 4.96 g (14.5 mmol) (R)-3-(2-chloro-5-iodo-pyrimidin-4-yloxy)-2-methyl-butan-2-ol in 30 ml DCM and stirred for 22 hours at room temperature. The mixture was diluted with DCM and washed with saturated sodium hydrogencarbonate solution. The organic phase was dried (Na₂SO₄), filtered and concentrated by evaporation. The residue obtained was purified chromatographically (hexane/ethyl acetate 4:1). 5.50 g (12.9 mmol; yield: 89%) of the mixture of diastereomers was obtained.

¹H-NMR (400 MHz, DMSO): δ=8.75 (s, 1H), 8.74 (s, 1H), 5.15 (m, 2H), 4.91 (m, 2H), 3.70 (m, 2H), 3.30 (m, 2H), 1.31 (m, 30H).

Compound 3.4

2-Chloro-4-[(R)-1,2-dimethyl-2-(tetrahydro-pyran-2-yloxy)-propoxy]-5-trifluoromethyl-pyrimidine

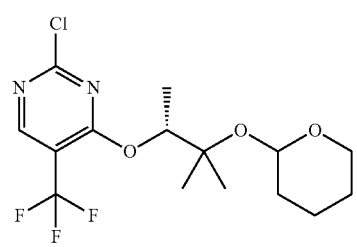 [SMILES: C[C@@H](Oc1nc(Cl)ncc1C(F)(F)F)C(C)(C)OC1CCCCO1]

1.61 g (8.44 mmol) of copper(I) iodide, 0.41 g (7.03 mmol) of potassium fluoride and 1.04 ml (7.03 mmol) of (trifluoromethyl)-trimethylsilane were added at room temperature to a solution of 1.00 g (2.34 mmol) of 2-chloro-4-[(R)-1,2-dimethyl-2-(tetrahydro-pyran-2-yloxy)-propoxy]-5-iodo-pyrimidine in 3.3 ml NMP and 3.3 ml THF. The mixture was stirred for 2 hours at 90° C. After cooling, the mixture was added to dilute sodium chloride solution and was extracted with ethyl acetate (3×). The combined organic phases were dried (Na₂SO₄), filtered and concentrated by evaporation. The residue obtained was purified chromatographically (hexane/ethyl acetate 4:1). 0.53 g (1.43 mmol; yield: 61%) of the product was obtained.

¹H-NMR (400 MHz, DMSO): δ=8.84 (s, 1H), 5.32 (m, 1H), 4.85 (m, 1H), 3.68 (m, 1H), 3.30 (m, 1H), 1.31 (m, 15H).

3b) Preparation of the End Product 200 mg (0.54 mmol) of 2-chloro-4-[(R)-1,2-dimethyl-2-(tetrahydro-pyran-2-yloxy)-propoxy]-5-trifluoromethyl-pyrimidine and 87 mg (0.33 mmol) of (RS)-S-(4-aminophenyl)-S-methyl-N-(trifluoroacetyl)sulfoximine in 5 ml ethanol were stirred for 6 hours at 70° C. The mixture was evaporated to dryness in a rotary evaporator and the residue was taken up in 11.6 ml. 373 mg (2.70 mmol) of potassium carbonate was added to the solution and it was stirred for 1.5 hours at room temperature. It was diluted with saturated sodium chloride solution and was extracted with ethyl acetate (2×). The combined organic phases were dried (Na₂SO₄), filtered and concentrated by evaporation. The residue was purified by HPLC. 31 mg (0.07 mmol; yield: 14%) of the product was obtained.

| Column: | XBridge C18 5µ 100 × 30 mm | | | |
|---|---|---|---|---|
| Eluent A: | H₂O/0.1% HCOOH | | | |
| Eluent B: | Acetonitrile | | | |
| Gradient: | 0 min | 70% A | 30% B | |
| | 1.00 min | 70% A | 30% B | |
| | 7.50 min | 40% A | 60% B | |
| | 7.52 min | 1% A | 99% B | |
| | 10.00 min | 1% A | 99% B | |
| Flow: | 50.0 mL/min | | | |
| Detection: | DAD scan range 210-400 nm; | | | |
| | MS ESI+, ESI−, scan range 160-1000 m/z | | | |
| Temperature: | RT | | | |

$^1$H-NMR (400 MHz, DMSO): δ=10.48 (s, 1H), 8.56 (s, 1H), 7.90 (m, 2H), 7.83 (m, 2H), 5.13 (q, 1H), 4.67 (s, 1H), 4.06 (s, 1H), 3.01 (s, 3H), 1.28 (d, 3H), 1.12 (m, 6H).

Preparation of the Compounds of General Formula (Ib) (4-N Derivatives)

The compounds according to the invention can be prepared by a method that is characterized by the following steps:

a) Oxidation of a compound of formula (IVd) to the sulfoxide of formula (IVc).

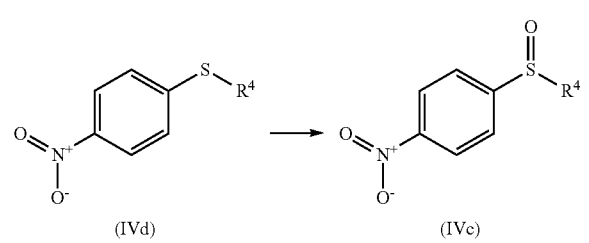

b$_1$) Direct imination of the sulfoxide of formula (IVc) to a protected sulfoximine of formula (IVa).

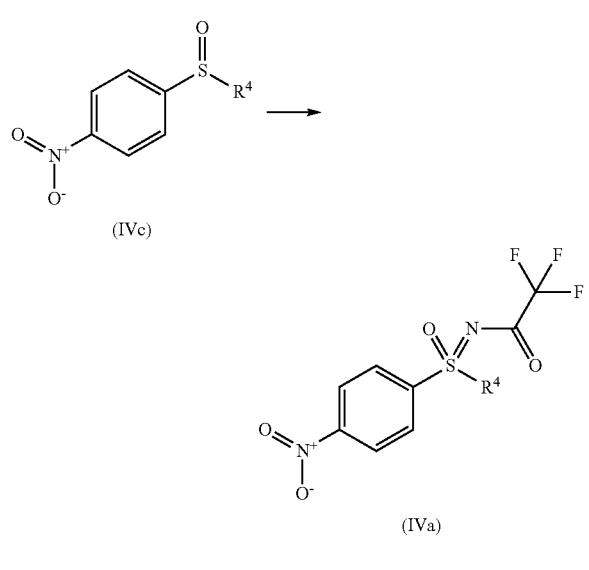

or b$_2$) Imination of the sulfoxide of formula (IVc) to an unprotected sulfoximine of formula (IVb) and subsequent introduction of the protective group to a compound of formula (IVa).

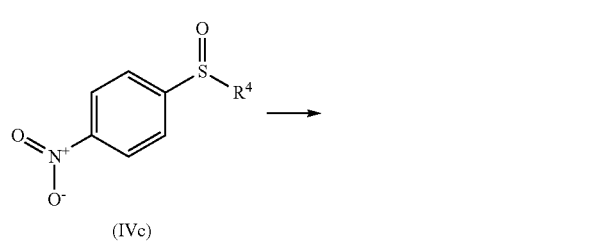

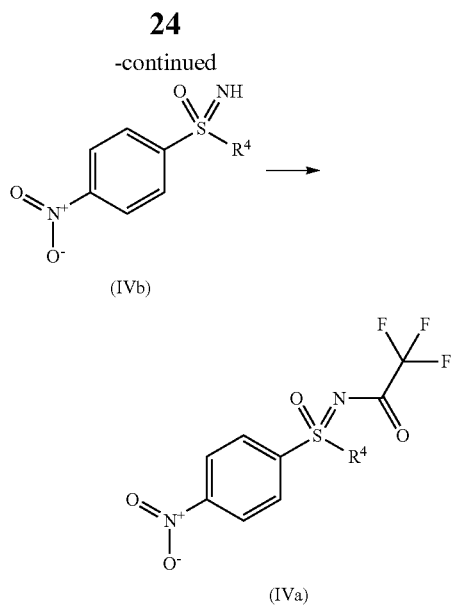

c) Reduction of the compound of formula (IVa) to a compound of formula (IV)

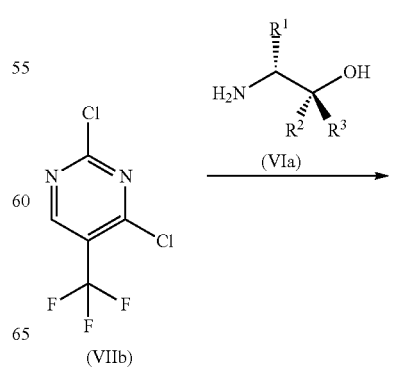

d) Functionalization of the 4-position of 2,4-dichloro-5-trifluoromethyl-pyrimidine (VIIb) by reaction with an amine of formula (VIa) with formation of an intermediate of formula (Vb).

-continued

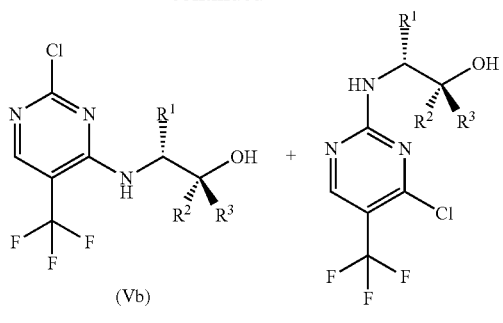

e) Coupling of the compounds of formula (Vb) and (IV) to the intermediate of formula (IIb).

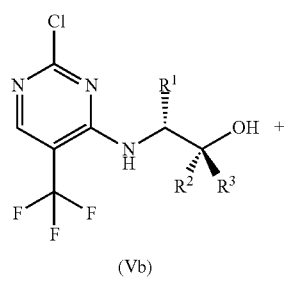

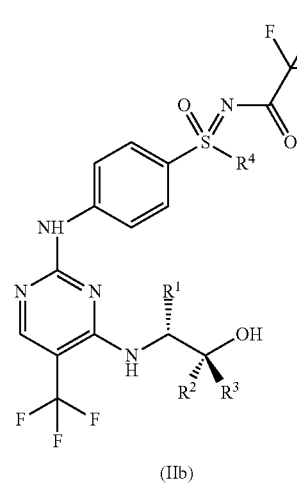

f) Cleavage of the protective group on the sulfoximine with formation of (Ib).

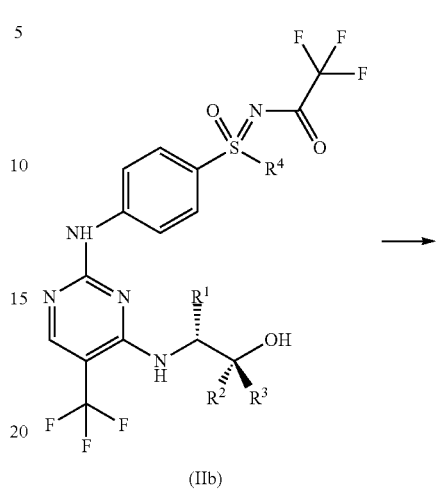

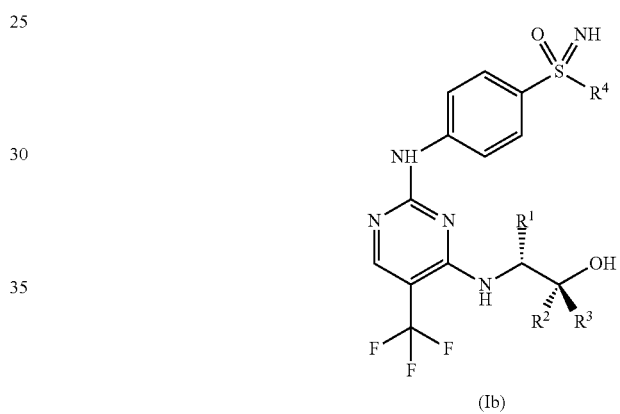

where the substituents $R^1$, $R^2$, $R^3$ and $R^4$ have the meanings given in general formula (I).

Steps a)-c)

These steps are identical to steps a)-d) for the preparation of compounds according to general formula (Ia).

Step d)

Reaction of 2,4-dichloro-5-trifluoromethyl-pyrimidine (VIIb) with an amine of formula (VIa) provides a mixture of products (Vb) and (Vc). The desired product (Vb) can be separated e.g. chromatographically (see e.g.: (a) J. Bryant et al., WO 2004/048343).

Step e)

A 2-chloro-pyrimidine of formula (Vb) can be reacted with an aniline of formula (IV) to an intermediate of formula (IIb) (see e.g.: (a) J. Bryant et al., WO 2004/048343).

Step f)

Cleavage of the trifluoroaceto group on the sulfoximine (IIb) provides the compound of formula (Ib). The technique described using potassium carbonate in methanol at room temperature is especially suitable for this.

EXAMPLE 4

(RS)-S-Cyclopropyl-S-(4-{[4-{[(1R,2R)-2-hydroxy-1-methylpropyl]amino}-5-(trifluoromethyl)pyrimidin-2-yl]amino}phenyl)sulfoximide

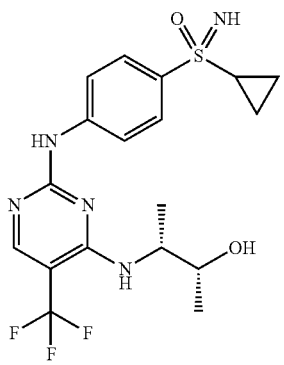

4a) Preparation of the Intermediates

Compound 4.1

(2R,3R)-3-(2-Chloro-5-trifluoromethyl-pyrimidin-4-ylamino)-butan-2-ol

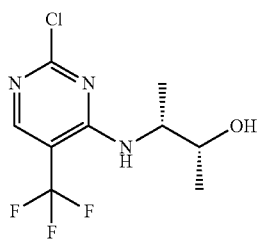 [SMILES: C[C@@H](O)[C@@H](C)Nc1nc(Cl)ncc1C(F)(F)F]

72.2 ml (520.71 mmol) triethylamine was added dropwise at 0° C. to 56.5 g (260.35 mmol) of 2,4-dichloro-5-trifluoromethyl-pyrimidine and 32.7 g (260.35 mmol) (2R,3R)-3-amino-butan-2-ol hydrochloride in 1035 ml acetonitrile. The mixture was heated slowly overnight to room temperature. The mixture was added to semiconcentrated sodium chloride solution and was extracted with ethyl acetate (2×). The combined organic phases were dried ($Na_2SO_4$), filtered and concentrated by evaporation. The residue that remained was purified chromatographically (hexane/ethyl acetate 0-100%). 18.6 g (68.97 mmol; yield: 27%) of the product was obtained.

$^1$H-NMR (400 MHz, DMSO): δ=8.38 (s, 1H), 6.71 (d, 1H), 5.00 (d, 1H), 4.08 (m, 1H), 3.71 (m, 1H), 1.12 (d, 3H), 1.01 (d, 3H).

The preparation of (RS)-S-(4-aminophenyl)-S-cyclopropyl-N-(trifluoroacetyl)sulfoximide was described as Compound 1.4.

4b) Preparation of the End Product 0.21 ml of 4N solution of hydrogen chloride in dioxane was added to 250 mg (0.86 mmol) of (RS)-S-(4-aminophenyl)-S-cyclopropyl-N-(trifluoroacetyl)sulfoximide and 231 mg (0.86 mmol) of (2R,3R)-3-(2-chloro-5-trifluoromethyl-pyrimidin-4-ylamino)-butan-2-ol in 3.75 ml acetonitrile and then stirred for 3.5 hours at 60° C. The mixture was evaporated to dryness. 18.4 ml methanol and 590 mg (4.28 mmol) of potassium carbonate were added and it was stirred for one hour at room temperature. It was diluted with saturated sodium chloride solution and was extracted with ethyl acetate (2×). The combined organic phases were dried ($Na_2SO_4$), filtered and concentrated by evaporation. The residue that remained was purified chromatographically (DCM/MeOH 4:1). 242 mg (0.56 mmol; yield: 65%) of the product was obtained.

$^1$H-NMR (400 MHz, DMSO): δ=10.04 (s, 1H), 8.25 (s, 1H), 7.91 (m, 2H), 7.74 (m, 2H), 6.05 (d, 1H), 5.07 (d, 1H), 4.14 (m, 1H), 3.97 (s, 1H), 3.77 (m, 1H), 2.56 (m, 1H), 1.19 (d, 3H), 1.05 (m, 4H), 0.86 (m, 3H).

MS: 430 (ESI+).

The mixture of diastereomers was separated into the pure stereoisomers by preparative HPLC:

Column: Chiralpak IA 5μ 250×20 mm

Eluents: Hexane/2-propanol 50:50

Buffer: Hexane/0.1% DEA

Flow: 15.0 mL/min

Detector: UV 254 nm

Temperature: Room temperature

Retention time: 5.9-6.6 min; stereoisomer 1 (=example 4-SI-1)

7.1-8.8 min; stereoisomer 2 (=example 4-SI-2)

EXAMPLE 5

(RS)-S-Cyclopropyl-S-(4-{[4-{[(R)-2-hydroxy-1,2-dimethylpropyl]amino}-5-(trifluoromethyl)pyrimidin-2-yl]amino}phenyl)sulfoximide

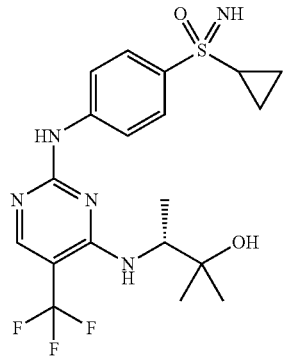 [SMILES: C[C@@H](Nc1nc(Nc2ccc(S(=N)(=O)C3CC3)cc2)ncc1C(F)(F)F)C(C)(C)O]

5a) Preparation of the Intermediates

Compound 5.1

(R)-3-(2-Chloro-5-trifluoromethyl-pyrimidin-4-ylamino)-2-methyl-butan-2-ol

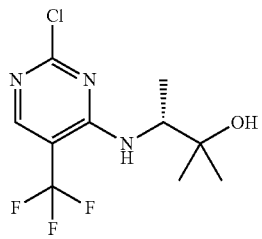 [SMILES: C[C@@H](Nc1nc(Cl)ncc1C(F)(F)F)C(C)(C)O]

3.6 g (35.03 mmol) of (R)-3-amino-2-methyl-butan-2-ol was added dropwise to a solution of 7.6 g (35.03 mmol) of 2,4-dichloro-5-trifluoromethyl-pyrimidine in 139 ml acetonitrile. 9.7 ml (70.1 mmol) triethylamine was now added dropwise at 0° C. and the mixture was heated slowly overnight to room temperature. It was stirred for a further 2 days at room temperature. The mixture was added to semiconcentrated sodium chloride solution and was extracted with ethyl acetate (2×). The combined organic phases were dried (Na$_2$SO$_4$), filtered and concentrated by evaporation. The residue that remained was purified by preparative HPLC. 3.0 g (10.65 mmol; yield: 30%) of the product was obtained.
Column: XBridge C18 5μ 150×20 mm
Eluent A: H$_2$O/0.2% NH$_3$
Eluent B: Acetonitrile
Gradient: 70% A+30% B(2') 30→60% B(10') 60→99% B(0.1')
Flow: 50.0 mL/min
Detector: DAD (200-400 nm) TAC; MS-ESI+ (160-1000 m/z) TIC
Temperature: Room temperature
Retention time: 5.6-6.4 min
$^1$H-NMR (400 MHz, DMSO): δ=8.42 (s, 1H), 6.52 (d, 1H), 5.01 (s, 1H), 4.10 (m, 1H), 1.11 (m, 9H).

The preparation of (RS)-S-(4-aminophenyl)-S-cyclopropyl-N-(trifluoroacetyl)sulfoximide was described as Compound 1.4.

5b) Preparation of the End Product 0.34 ml of 4N solution of hydrogen chloride in dioxane was added to 400 mg (1.37 mmol) (RS)-S-(4-aminophenyl)-S-cyclopropyl-N-(trifluoroacetyl)sulfoximide and 388 mg (1.37 mmol) (R)-3-(2-chloro-5-trifluoromethyl-pyrimidin-4-ylamino)-2-methyl-butan-2-ol in 6.0 ml acetonitrile and stirred for 3.5 hours at 60° C. The mixture was evaporated to dryness. 29.4 ml methanol and 950 mg (6.84 mmol) of potassium carbonate were added and it was stirred for one hour at room temperature. It was diluted with saturated sodium chloride solution and was extracted with ethyl acetate (2×). The combined organic phases were dried (Na$_2$SO$_4$), filtered and concentrated by evaporation. 600 mg (1.35 mmol) of the raw product was obtained.
$^1$H-NMR (400 MHz, DMSO): δ=10.08 (s, 1H), 8.30 (s, 1H), 7.94 (m, 2H), 7.80 (m, 2H), 6.07 (d, 1H), 4.95 (s, 1H), 4.16 (m, 1H), 4.02 (s, 1H), 2.62 (m, 1H), 1.20 (m, 6H), 1.10 (m, 4H), 0.89 (m, 3H).

MS: 444 (ESI+).

The mixture of diastereomers was separated into the pure stereoisomers by preparative HPLC:
Column: Chiralpak AD-H 5μ 250×20 mm
Eluents: Hexane/2-propanol 60:40
Buffer: Hexane/0.1% DEA
Flow: 20.0 mL/min
Detector: UV 280 nm
Temperature: Room temperature
Retention time: 5.1-6.3 min; stereoisomer 1 (=example 5-SI-1)
8.0-10.8 min; stereoisomer 2 (=example 5-SI-2)

EXAMPLE 6

(RS)-S-Ethyl-S-(4-{[4-{[(1R,2R)-2-hydroxy-1-methylpropyl]amino}-5-(trifluoromethyl)pyrimidin-2-yl]amino}phenyl)sulfoximide

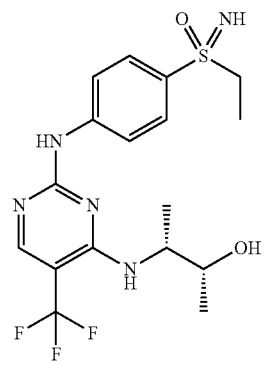 [SMILES: CCS(=N)(=O)c1ccc(Nc2ncc(C(F)(F)F)c(N[C@H](C)[C@@H](C)O)n2)cc1]

6a) Preparation of the Intermediates

Compound 6.1

1-Ethylsulfanyl-4-nitrobenzene

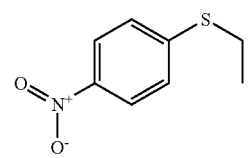

16.56 g (106.72 mmol) of 4-nitrothiophenol was added, while cooling with water, to a solution of 4.27 g (106.76 mmol) sodium hydroxide in 320 ml ethanol and it was stirred for 15 minutes at room temperature. Then, while cooling with water, 8.63 ml (106.79 mmol) of ethyl iodide was added and the mixture was stirred overnight at room temperature. The mixture was added to saturated sodium chloride solution and was extracted with ethyl acetate (2×). The combined organic phases were dried (Na$_2$SO$_4$), filtered and concentrated by evaporation. Then it was dissolved in DCM and filtered again and evaporated to dryness. 16.86 g (92.02 mmol) of the raw product was obtained.

¹H-NMR (400 MHz, DMSO): δ=8.14 (m, 2H), 7.49 (m, 2H), 3.14 (q, 2H), 1.31 (tr, 3H).

Compound 6.2

(RS)-1-Ethylsulfinyl-4-nitrobenzene

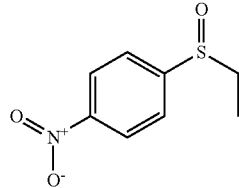

428 mg (2.64 mmol) of iron(III) chloride was added to a mixture of 16.86 g (92.02 mmol) of 1-ethylsulfanyl-4-nitrobenzene in 75 ml acetonitrile and it was stirred for 10 minutes at room temperature. Then 22.44 g (98.44 mmol) of periodic acid was added in portions, so that the temperature did not exceed 30° C. The mixture was stirred for 50 minutes and was then added, with stirring, to a mixture of 170 ml DCM, 500 ml ice water and 100 g sodium thiosulfate pentahydrate. It was extracted with DCM (2×). The combined organic phases were dried (Na₂SO₄), filtered and concentrated by evaporation. The residue obtained was recrystallized from ethyl acetate/hexane. 12.49 g (62.69 mmol; yield: 68%) of the product was obtained.

¹H-NMR (400 MHz, DMSO): δ=8.35 (m, 2H), 7.88 (m, 2H), 3.12 (m, 1H), 2.84 (m, 1H), 0.99 (tr, 3H).

Compound 6.3

(RS)-S-Ethyl-S-(4-nitrophenyl)sulfoximide

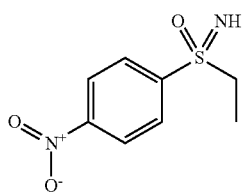

30.5 ml of oleum (20% SO₃) was added carefully, on an ice bath, to 6.00 g (30.12 mmol) of (RS)-1-ethylsulfinyl-4-nitrobenzene. Then, under argon, 2.35 g (36.14 mmol) of sodium azide was added carefully, in portions and with stirring, and the mixture was heated to 45° C. After 6 hours the mixture was cooled to room temperature and carefully poured onto ice. The mixture was alkalized with sodium hydrogencarbonate and was extracted with ethyl acetate (2×). The combined organic phases were dried (Na₂SO₄), filtered and concentrated by evaporation. 5.74 g (26.79 mmol; yield: 89%) of the product was obtained.

¹H-NMR (400 MHz, DMSO): δ=8.37 (m, 2H), 8.09 (m, 2H), 4.56 (s, 1H), 3.18 (q, 2H), 1.04 (tr, 3H).

Compound 6.4

(RS)-S-Ethyl-S-(4-nitrophenyl)-N-(trifluoroacetyl) sulfoximide

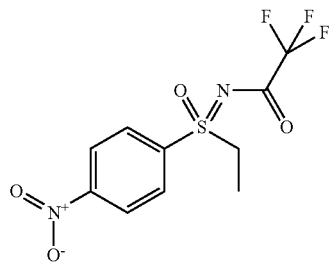 [SMILES: CCS(=O)(=NC(=O)C(F)(F)F)c1ccc([N+](=O)[O-])cc1]

4.53 ml (32.04 mmol) of trifluoroacetic anhydride was added dropwise, with ice cooling, to a solution of 5.72 g (26.70 mmol) (RS)-S-ethyl-S-(4-nitrophenyl)sulfoximide and 4.07 ml (29.37 mmol) triethylamine in 175 ml DCM. The mixture was stirred for a further 3 hours on the ice bath, wherein the temperature rose to approx. 10° C. It was diluted with DCM and washed with semiconcentrated sodium chloride solution. The organic phase was dried (Na₂SO₄), filtered and concentrated by evaporation. 8.17 g (26.33 mmol) of the product was obtained.

¹H-NMR (400 MHz, DMSO): δ=8.52 (m, 2H), 8.22 (m, 2H), 3.99 (m, 2H), 1.16 (tr, 3H).

Compound 6.5

(RS)-S-(4-Aminophenyl)-S-ethyl-N-(trifluoroacetyl) sulfoximide

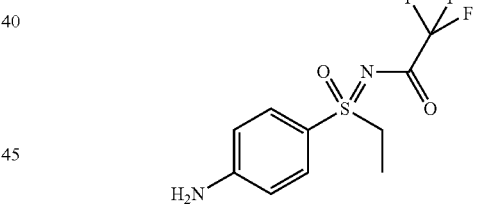

88.5 ml of 15% solution of titanium(III) chloride in approx. 10% hydrochloric acid was added slowly, with ice cooling, to a solution of 4.05 g (13.05 mmol) (RS)-S-ethyl-S-(4-nitrophenyl)-N-(trifluoroacetyl)sulfoximide in 191 ml THF. The mixture was stirred for 3.5 hours at room temperature, diluted with ethyl acetate and then washed with semiconcentrated sodium chloride solution (3×). The organic phase was dried (Na₂SO₄), filtered and concentrated by evaporation. 3.17 g (11.31 mmol) of the product was obtained.

¹H-NMR (400 MHz, DMSO): δ=7.48 (m, 2H), 6.68 (m, 2H), 3.64 (m, 2H), 1.06 (tr, 3H).

The preparation of (2R,3R)-3-(2-chloro-5-trifluoromethyl-pyrimidin-4-ylamino)-butan-2-ol was described as Compound 4.1.

6b) Preparation of the End Product 0.36 ml of 4N solution of hydrogen chloride in dioxane was added to 400 mg (1.43 mmol) (RS)-S-(4-aminophenyl)-S- ethyl-N-(trifluoroacetyl)sulfoximide and 385 mg (1.43 mmol) (2R,3R)-3-(2-chloro-5-trifluoromethyl-pyrimidin-4-ylamino)-butan-2-ol in 7.0 ml acetonitrile and stirred for 4.5 hours at 60° C. The mixture was evaporated to dryness. 19.0 ml methanol and 608 mg (4.40 mmol) of potassium carbonate were added, and it was stirred for 1 hour at room temperature. It was diluted with saturated sodium chloride solution and was extracted with ethyl acetate (2×). The combined organic phases were dried ($Na_2SO_4$), filtered and concentrated by evaporation. 590 mg (1.41 mmol) of the raw product was obtained.

$^1$H-NMR (400 MHz, DMSO): δ=10.10 (s, 1H), 8.30 (s, 1H), 7.96 (m, 2H), 7.78 (m, 2H), 6.10 (d, 1H), 5.11 (d, 1H), 4.19 (m, 1H), 4.00 (s, 1H), 3.82 (m, 1H), 3.07 (q, 2H), 1.24 (d, 3H), 1.06 (m, 6H).

MS: 418 (ESI+).

The mixture of diastereomers was separated into the pure stereoisomers by preparative HPLC:
Column: Chiralpak AD-H 5μ 250×20 mm
Eluents: Hexane/2-propanol 60:40
Buffer: Hexane/0.1% DEA
Flow: 20.0 mL/min
Detector: UV 280 nm
Temperature: Room temperature
Retention time: 6.2-6.8 min; stereoisomer 1 (=example 6-SI-1)
7.2-8.9 min; stereoisomer 2 (=example 6-SI-2)

EXAMPLE 7

(RS)-S-Ethyl-S-(4-{[4-{[(R)-2-hydroxy-1,2-dimethylpropyl]amino}-5-(trifluoromethyl)pyrimidin-2-yl]amino}phenyl)sulfoximide

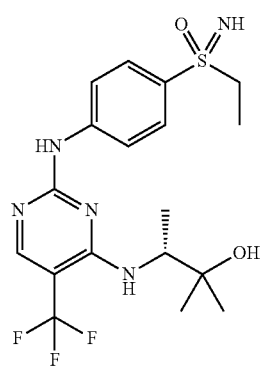 [SMILES: CCS(=N)(=O)c1ccc(Nc2ncc(C(F)(F)F)c(N[C@H](C)C(C)(C)O)n2)cc1]

7a) Preparation of the Intermediates

The preparation of (RS)-S-(4-aminophenyl)-S-ethyl-N-(trifluoroacetyl)sulfoximide was described as Compound 6.5.

The preparation of (R)-3-(2-chloro-5-trifluoromethyl-pyrimidin-4-ylamino)-2-methyl-butan-2-ol was described as Compound 5.1.

7b) Preparation of the End Product 0.36 ml of 4N solution of hydrogen chloride in dioxane was added to 400 mg (1.43 mmol) of (RS)-S-(4-aminophenyl)-S-ethyl-N-(trifluoroacetyl)sulfoximide and 405 mg (1.43 mmol) of (R)-3-(2-chloro-5-trifluoromethyl-pyrimidin-4-ylamino)-2-methyl-butan-2-ol in 7.0 ml acetonitrile and stirred for 4.5 hours at 60° C. The mixture was evaporated to dryness. 25.0 ml methanol and 788 mg (5.70 mmol) of potassium carbonate were added and it was stirred for one hour at room temperature. It was diluted with saturated sodium chloride solution and was extracted with ethyl acetate (2×). The combined organic phases were dried ($Na_2SO_4$), filtered and concentrated by evaporation. 620 mg (1.43 mmol) of the raw product was obtained.

$^1$H-NMR (400 MHz, DMSO): δ=10.06 (s, 1H), 8.28 (s, 1H), 7.92 (m, 2H), 7.74 (m, 2H), 6.03 (d, 1H), 4.90 (s, 1H), 4.12 (m, 1H), 3.96 (s, 1H), 3.03 (q, 2H), 1.16 (m, 6H), 1.08 (m, 3H), 1.02 (tr, 3H).

MS: 432 (ESI+).

The mixture of diastereomers was separated into the pure stereoisomers by preparative HPLC:
Column: Chiralpak AD-H 5μ 250×20 mm
Eluents : A:Hexane B:2-propanol
Buffer: Hexane/0.1% DEA
Gradient: 20→40% B(20')+40% B(5')
Flow: 10.0 mL/min
Detector: UV 280 nm
Temperature: Room temperature
Retention time: 17.5-19.8 min; stereoisomer 1 (=example 7-SI-1)
20.1-22.0 min; stereoisomer 2 (=example 7-SI-2)

EXAMPLE 8

(RS)-S-(4-{[4-{[(1 R,2R)-2-Hydroxy-1-methylpropyl]amino}-5-(trifluoromethyl)pyrimidin-2-yl]amino}phenyl)-S-methylsulfoximide

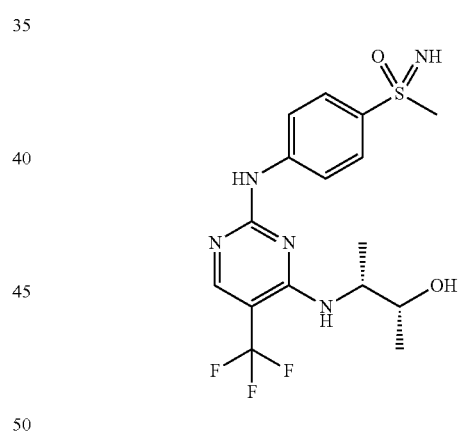

8a) Preparation of the Intermediates

The preparation of (RS)-S-(4-aminophenyl)-S-methyl-N-(trifluoroacetyl)sulfoximide was described as Compound 2.3.

The preparation of (2R,3R)-3-(2-chloro-5-trifluoromethyl-pyrimidin-4-ylamino)-butan-2-ol was described as Compound 4.1.

8b) Preparation of the End Product 0.38 ml of 4N solution of hydrogen chloride in dioxane was added to 399 mg (1.50 mmol) of (RS)-S-(4-aminophenyl)-S-methyl-N-(trifluoroacetyl)sulfoximide and 404 mg (1.50 mmol) of (2R,3R)-3-(2-chloro-5-trifluoromethyl-pyrimidin-4-ylamino)-butan-2-ol in 7.3 ml acetonitrile and stirred for 9 hours at 60° C. The mixture was evaporated to dryness. 32.2 ml methanol and 1040 mg (7.50 mmol) of potassium carbonate were added and it was stirred for 1.5 hours at room temperature. It was diluted with saturated sodium chloride solution and was extracted with ethyl acetate (3×). The combined organic phases were dried ($Na_2SO_4$), filtered and concentrated by evaporation. 565 mg (1.40 mmol) of the raw product was obtained.

$^1$H-NMR (400 MHz, DMSO): 10.09 (s, 1H), 8.30 (s, 1H), 7.96 (m, 2H), 7.83 (m, 2H), 6.10 (d, 1H), 5.11 (d, 1H), 4.18 (m, 1H), 4.03 (s, 1H), 3.82 (m, 1H), 3.03 (s, 3H), 1.25 (d, 3H), 1.10 (d, 3H).

The mixture of diastereomers was separated into the pure stereoisomers by preparative HPLC:
Column: Chiralpak IC 5µ 250×20 mm
Eluents: Hexane/ethanol 50:50
Buffer: Hexane/0.1% DEA
Flow: 20.0 mL/min
Detector: UV 254 nm
Temperature: Room temperature
Retention time: 5.1-5.8 min; stereoisomer 1 (=example 8-SI-1)
6.1-6.7 min; stereoisomer 2 (=example 8-SI-2)

EXAMPLE 9

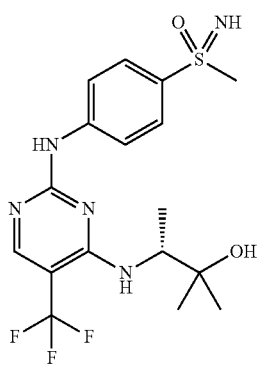 [SMILES: C[C@@H](Nc1nc(Nc2ccc(S(C)(=N)=O)cc2)ncc1C(F)(F)F)C(C)(C)O]

9a) Preparation of the Intermediates

The preparation of (RS)-S-(4-aminophenyl)-S-methyl-N-(trifluoroacetyl)sulfoximide was described as Compound 2.3.

The preparation of (R)-3-(2-chloro-5-trifluoromethyl-pyrimidin-4-ylamino)-2-methyl-butan-2-ol was described as Compound 5.1.

9b) Preparation of the End Product 0.38 ml of 4N solution of hydrogen chloride in dioxane was added to 399 mg (1.50 mmol) of (RS)-S-(4-aminophenyl)-S-methyl-N-(trifluoroacetyl)sulfoximide and 425 mg (1.50 mmol) of (R)-3-(2-chloro-5-trifluoromethyl-pyrimidin-4-ylamino)-2-methyl-butan-2-ol in 7.3 ml acetonitrile and it was stirred for 4 hours at 60° C. The mixture was evaporated to dryness. 32.2 ml methanol and 1040 mg (7.50 mmol) of potassium carbonate were added and it was stirred for 1.5 hours at room temperature. It was diluted with saturated sodium chloride solution and was extracted with ethyl acetate (2×). The combined organic phases were dried ($Na_2SO_4$), filtered and concentrated by evaporation. 600 mg (1.44 mmol) of the raw product was is obtained.

$^1$H-NMR (400 MHz, DMSO): δ=10.05 (s, 1H), 8.26 (s, 1H), 7.91 (m, 2H), 7.79 (m, 2H), 6.03 (d, 1H), 4.91 (s, 1H), 4.11 (m, 1H), 3.99 (s, 1H), 2.99 (s, 3H), 1.16 (m, 6H), 1.10 (m, 3H).

MS: 418 (ESI+).

The mixture of diastereomers was separated into the pure stereoisomers by preparative HPLC:
Column: Chiralpak IC 5µ 250×20 mm
Eluents: Hexane/ethanol 80:20
Flow: 30.0 mL/min
Detector: UV 254 nm
Temperature: Room temperature
Retention time: 6.0-6.7 min; stereoisomer 1 (=example 9-SI-1)
7.1-8.9 min; stereoisomer 2 (=example 9-SI-2)

Preparation of the Comparative Substances

The compounds according to the invention, characterized inter alia by a 5-$CF_3$ substituent in position 5 of the pyrimidine, were compared, with respect to in-vitro and in-vivo efficacy, with their 5-Br analogs that were either disclosed explicitly in WO 2005/037800 or alternatively are covered by its generic disclosure.

V11=5-Br Comparative Substance in Example 11

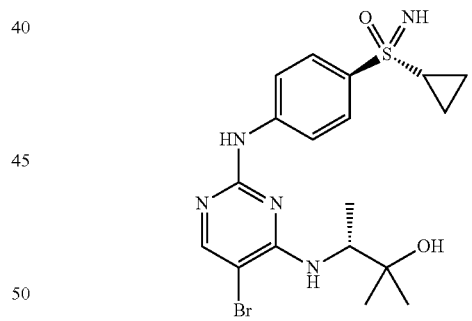

The comparative substance in example 11 is the more active stereoisomer of the mixture of diastereomers (RS)-S-[4-({5-bromo-4-[(R)-(2-hydroxy-1,2-dimethylpropyl)amino]pyrimidin-2-yl}amino)phenyl]-S-cyclopropyl-sulfoximide, which is disclosed as example 1.6 in application WO 2005/037800 (p. 35). For the comparison in-vivo, the diastereomer (R)-S-[4-({5-bromo-4-[(R)-(2-hydroxy-1,2-dimethylpropyl)amino]pyrimidin-2-yl}amino)phenyl]-S-cyclopropyl-sulfoximide, which has higher in-vitro efficacy than (S)-S-[4-({5-bromo-4-[(R)-(2-hydroxy-1,2-dimethylpropyl)amino]pyrimidin-2-yl}amino)phenyl]-S-cyclopropyl-sulfoximide, was used in example 11.

For this purpose, V11 was prepared by the following method:

V11a) Preparation of the Intermediate

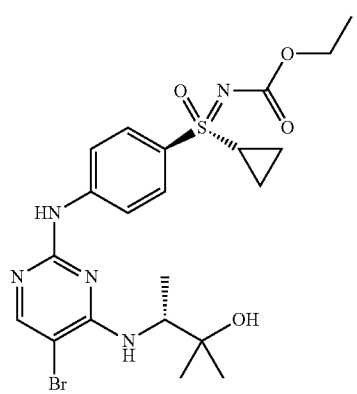

0.07 ml of 4N solution of hydrogen chloride in dioxane was added to 988 mg (3.35 mmol) of (R)-3-(5-bromo-2-chloro-pyrimidin-4-ylamino)-2-methyl-butan-2-ol and 750 mg (2.79 mmol) (R)-S-(4-aminophenyl)-N-(ethoxycarbonyl)-S-cyclopropylsulfoximide (preparation according to: U. Lucking et al., WO 2007/071455, p. 112, Example 4) in 16.50 ml butanol and 1.65 ml methanol and was stirred for 3 days at 60° C. After cooling, the mixture was evaporated to dryness and purified chromatographically (DCM/EtOH 9:1). 319 mg (0.61 mmol, yield: 22%) of the product was obtained.

$^1$H-NMR (400 MHz, DMSO): δ=9.96 (s, 1H), 8.13 (s, 1H), 7.92 (m, 2H), 7.73 (m, 2H), 6.28 (d, 1H), 4.05 (m, 1H), 3.84 (m, 2H), 2.96 (m, 1H), 1.05 (m, 16H).

V11 b) Preparation of the End Product 2.0 ml of freshly prepared 1.5M sodium ethanolate solution was added to 319 mg (0.61 mmol) of the intermediate in 4.3 ml ethanol and stirred for 18 hours at 60° C. After cooling, the mixture was added to saturated sodium chloride solution and was extracted with ethyl acetate (3×). The combined organic phases were dried (Na$_2$SO$_4$), filtered and concentrated by evaporation. After final recrystallization (DCM/ethyl acetate), 215 mg (0.47 mmol; yield: 78%) of the product was obtained.

$^1$H-NMR (400 MHz, DMSO): δ=9.68 (s, 1H), 8.08 (s, 1H), 7.86 (m, 2H), 7.70 (m, 2H), 6.07 (d, 1H), 4.82 (s, 1H), 4.05 (m, 1H), 3.93 (s, 1H), 2.55 (m, 1H), 1.15 (m, 6H), 1.10 (m, 3H), 1.03 (m, 1H), 0.83 (m, 3H).

Column: Chiralpak AD-H 5μ 150×4.6 mm

Eluents: Hexane/ethanol 80.20

Flow: 1.0 mL/min

Detection: PDA 280 nm

Temperature: 25° C.

Retention time: 11.64 min

V12 =5-Br Comparative Substance in Example 12

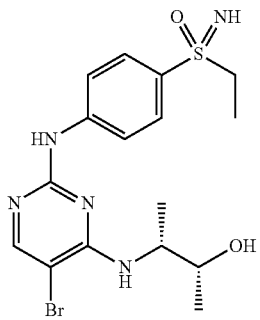 [SMILES: CCS(=N)(=O)c1ccc(Nc2ncc(Br)c(N[C@H](C)[C@@H](C)O)n2)cc1]

The comparative substance in example 12 was prepared according to example 1.52 in WO 2005/037800. Example 1.52 has a greater in-vitro efficacy than example 1.53.

V13=5-Br Comparative Substance in Example 13

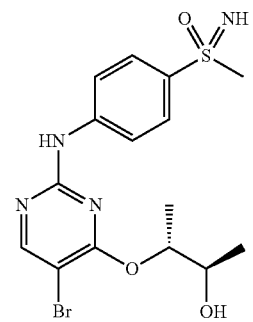 [SMILES: C[C@@H](O)[C@@H](C)Oc1nc(Nc2ccc(S(C)(=N)=O)cc2)ncc1Br]

The comparative substance in example 13 was prepared according to example 3.13 in WO 2005/037800. Example 3.13 has a greater in-vitro efficacy than example 3.12.

V14=5-Br Comparative Substance in Example 14

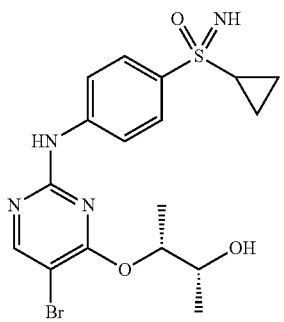 [SMILES: C[C@@H](O)[C@@H](C)Oc1nc(Nc2ccc(S(=N)(=O)C3CC3)cc2)ncc1Br]

V14a) Preparation of the Intermediate

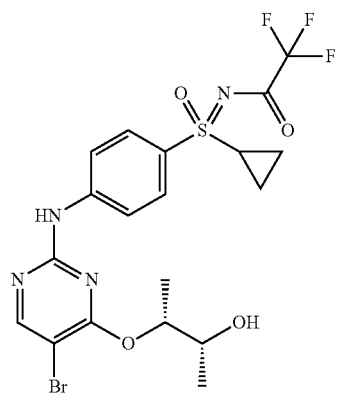 [SMILES: C[C@@H](O)[C@@H](C)Oc1nc(Nc2ccc(S(=O)(=NC(=O)C(F)(F)F)C3CC3)cc2)ncc1Br]

1.5 ml of 4N solution of hydrogen chloride in dioxane was added to 845 mg (3.00 mmol) of (2R,3R)-3-(5-bromo-2-chloro-pyrimidin-4-yloxy)-butan-2-ol (preparation according to: WO 2005/037800, p. 93) and 877 mg (3.00 mmol) of (RS)-S-(4-aminophenyl)-S-cyclopropyl-N-(trifluoroacetyl) sulfoximide in 13.1 ml acetonitrile and stirred for 5 hours at 80° C. A further 422 mg (1.50 mmol) of (2R,3R)-3-(5-bromo-2-chloro-pyrimidin-4-yloxy)-butan-2-ol was added to the mixture and it was stirred further at 80° C. After 3 hours, 0.75 ml of 4N solution of hydrogen chloride in dioxane was added again and stirred further at 80° C. After 33 hours, 175 mg (0.60 mmol) of (RS)-S-(4-aminophenyl)-S-cyclopropyl-N-(trifluoroacetyl)sulfoximide was added again and it was stirred finally for 18 hours at 80° C.

After cooling, the mixture was concentrated by evaporation and the residue that remained was purified chromatographically (DCM/EtOH 9:1). 740 mg (1.38 mmol, yield: 46%) of the product was obtained.

$^1$H-NMR (400 MHz, DMSO): δ=10.31 (s, 1H), 8.44 (s, 1H), 8.01 (m, 2H), 7.84 (m, 2H), 5.19 (m, 1H), 4.88 (d, 1H), 3.81 (m, 1H), 3.31 (m, 1H), 1.40 (m, 1H), 1.29 (m, 4H), 1.08 (m, 5H).

V14b) Preparation of the End Product 950 mg (6.84 mmol) of potassium carbonate was added to 735 mg (1.37 mmol) of the intermediate in 29 ml methanol and it was stirred for 1.5 hours at room temperature. It was diluted with saturated sodium chloride solution and was extracted with ethyl acetate (3×). The combined organic phases were dried ($Na_2SO_4$), filtered and concentrated by evaporation. 607 mg (1.37 mmol) of the raw product was obtained.

$^1$H-NMR (400 MHz, DMSO): δ=10.08 (s, 1H), 8.40 (s, 1H), 7.86 (m, 2H), 7.75 (m, 2H), 5.19 (m, 1H), 4.87 (d, 1H), 3.97 (s, 1H), 3.82 (m, 1H), 2.56 (m, 1H), 1.25 (d, 3H), 1.09 (d, 3H), 1.05 (m, 1H), 0.86 (m, 3H).

The mixture of diastereomers was separated into the pure stereoisomers by preparative HPLC:
Column: Chiralpak IC 5μ 250×20 mm
Eluents: Hexane/ethanol 7:3
Flow: 20.0 mL/min
Detector: UV 280 nm
Temperature: Room temperature
Retention time: 9.6-11.2 min; stereoisomer 1
11.3-14.9 min; stereoisomer 2

Stereoisomer 2 showed greater in-vitro efficacy than stereoisomer 1 and was therefore used as comparative substance in example 14.

EXAMPLE 10

10.1 Assay 1: CDK1/CycB Kinase Assay

Recombinant CDK1 and CycB-GST fusion proteins, purified from baculovirus-infected insect cells (Sf9), were purchased from ProQinase GmbH, Freiburg. The histon IIIS used as kinase substrate is commercially available from the company Sigma.

CDK1/CycB (200 ng/measuring point) was incubated for 10 min at 22° C. in the presence of various concentrations of test substances (0 μM, and within the range 0.01-100 μM) in assay buffer [50 mM Tris/HCl pH8.0, 10 mM $MgCl_2$, 0.1 mM Na ortho-vanadate, 1.0 mM dithiothreitol, 0.5 μM adenosine triphosphate (ATP), 10 μg/measuring point histon IIIS, 0.2 μCi/measuring point $^{33}$P-gamma ATP, 0.05% NP40, 1.25% dimethylsulfoxide]. The reaction was stopped by adding EDTA solution (250 mM, pH8.0, 15 μl/measuring point).

From each reaction mixture, 15 μl was applied to P30 filter strips (from Wallac), and unincorporated $^{33}$P-ATP was removed by washing the filter strips three times, for 10 min each time, in 0.5% phosphoric acid. After drying the filter strips for 1 hour at 70° C., the filter strips were covered with scintillator strips (MeltiLex™ A, from Wallac) and stoved for 1 hour at 90° C. The amount of incorporated $^{33}$P (substrate phosphorylation) was determined by scintillation measurement in a gamma-radiation measuring instrument (Wallac). The measured data were standardized to 0% inhibition (enzyme reaction without inhibitor) and 100% inhibition (all assay components except enzyme). The $IC_{50}$ values were determined by means of a 4-parameter fit using the company's own software.

10.2 Assay 2: CDK2/CycE Kinase Assay

Recombinant CDK2 and CycE-GST fusion proteins, purified from baculovirus-infected insect cells (Sf9), were purchased from ProQinase GmbH, Freiburg. Histon IIIS, used as kinase substrate, was purchased from the company Sigma. CDK2/CycE (50 ng/measuring point) was incubated for 10 min at 22° C. in the presence of various concentrations of test substances (0 μM, and within the range 0.01-100 μM) in assay buffer [50 mM Tris/HCl pH8.0, 10 mM $MgCl_2$, 0.1 mM Na ortho-vanadate, 1.0 mM dithiothreitol, 0.5 μM adenosine triphosphate (ATP), 10 μg/measuring point histon IIIS, 0.2 μCi/measuring point $^{33}$P-gamma ATP, 0.05% NP40, 1.25% dimethylsulfoxide]. The reaction was stopped by adding EDTA solution (250 mM, pH8.0, 15 μl/measuring point).

From each reaction mixture, 15 μl was applied to P30 filter strips (from Wallac), and unincorporated $^{33}$P-ATP was removed by washing the filter strips three times, for 10 min each time, in 0.5% phosphoric acid. After drying the filter strips for 1 hour at 70° C., the filter strips were covered with scintillator strips (MeltiLex™ A, from Wallac) and stoved for 1 hour at 90° C. The amount of incorporated $^{33}$P (substrate phosphorylation) was determined by scintillation measurement in a gamma-radiation measuring instrument (Wallac). The measured data were standardized to 0% inhibition (enzyme reaction without inhibitor) and 100% inhibition (all assay components except enzyme). The $IC_{50}$ values were determined by means of a 4-parameter fit using the company's own software.

10.3 Assay 3: VEGF Receptor-2 Kinase Assay

Recombinant VEGF receptor tyrosine kinase-2 was purified as GST fusion protein from baculovirus-infected insect cells (Sf9). Poly-(Glu4Tyr), used as kinase substrate, was purchased from the company Sigma.

VEGF receptor tyrosine kinase (90 ng/measuring point) was incubated for 10 min at 22° C. in the presence of various concentrations of test substances (0 μM, and within the range 0.001-30 μM) in 30 μl assay buffer [40 mM Tris/HCl pH5.5, 10 mM $MgCl_2$, 1 mM $MnCl_2$, 3 μM Na ortho-vanadate, 1.0 mM dithiothreitol, 8 μM adenosine triphosphate (ATP), 0.96 μg/measuring point poly-(Glu4Tyr), 0.2 μCi/measuring point $^{33}$P-gamma ATP, 1.4% dimethylsulfoxide]. The reaction was stopped by adding EDTA solution (250 mM, pH8.0, 15 μl/measuring point).

From each reaction mixture, 15 μl was applied to P30 filter strips (from Wallac), and unincorporated $^{33}$P-ATP was removed by washing the filter strips three times, for 10 min each time, in 0.5% phosphoric acid. After drying the filter strips for 1 hour at 70° C., the filter strips were covered with scintillator strips (MeltiLex™ A, from Wallac) and stoved for 1 hour at 90° C. The amount of incorporated $^{33}$P (substrate phosphorylation) was determined by scintillation measurement in a gamma-radiation measuring instrument (Wallac). The measured data were standardized to 0% inhibition (enzyme reaction without inhibitor) and 100% inhibition (all assay components except enzyme). The $IC_{50}$ values were determined by means of a 4-parameter fit using the company's own software.

10.4 Assay 4: Proliferation Assay

Cultivated human HeLa-MaTu cervical carcinoma cells (obtained from EPO-GmbH, Berlin) were plated at a density of 3000 cells/measuring point in a 96-well multititer is plate in 200 μl of growth medium (DMEM/HAMS F12, 2 mM L-glutamine, 10% fetal calf serum). After 24 hours the cells of one plate (zero-point plate) were stained with crystal violet (see below), whereas the medium of the other plates was replaced with fresh culture medium (200 μl), to which the test substances had been added at various concentrations (0 μM, and in the range 0.01-30 μM; the final concentration of the solvent dimethylsulfoxide was 0.5%). The cells were incubated for 4 days in the presence of the test substances. Cellular proliferation was determined by staining the cells with crystal violet: the cells were fixed by adding 20 μl/measuring point of an 11% glutaraldehyde solution for 15 min at room temperature. After washing the fixed cells with water three times, the plates were dried at room temperature. The cells were stained by adding 100 μl/measuring point of a 0.1% crystal violet solution (pH adjusted to pH3 by adding acetic acid). After washing the stained cells with water three times, the plates were dried at room temperature. The dye was dissolved by adding 100 μl/measuring point of a 10% acetic acid solution. The extinction was determined photometrically at a wavelength of 595 nm. The percentage change in cell growth was calculated by standardization of the measured values to the extinction values of the zero-point plate (=0%) and the extinction of the untreated (0 μM) cells (=100%). The measured data were standardized to 0% inhibition (cell proliferation without inhibitor) and 100% inhibition (zero-point plate). The $IC_{50}$ values were determined by means of a 4-parameter fit using the company's own software.

10.5 Results from the Enzyme and Proliferation Assays

TABLE 1

| Example | CDK1/CycB (Assay 1) | CDK2/CycE (Assay 2) | VEGF-R2 (Assay 3) | HeLa-MaTu (Assay 4) |
|---|---|---|---|---|
| | Concentration for 50% inhibition of enzyme activity or cellular proliferation, $IC_{50}$ [nM] | | | |
| 1-SI-1 | 9 | 7 | 114 | 13 |
| 1-SI-2 | 7 | 9 | 163 | 11 |
| 2-SI-1 | 5 | 6 | 84 | 12 |
| 2-SI-2 | 4 | 5 | 281 | 8 |
| 3 | 13 | 10 | | 70 |
| 4-SI-1 | 6 | 6 | 46 | 10 |
| 4-SI-2 | | | | |
| 5-SI-1 | 25 | 8 | 70 | 22 |
| 5-SI-2 | 9 | 8 | 82 | 10 |
| 6-SI-1 | 10 | 5 | 73 | 16 |
| 6-SI-2 | 5 | 5 | 71 | 10 |
| 7-SI-1 | 24 | 4 | 143 | 27 |
| 7-SI-2 | 7 | 5 | 136 | 10 |
| 8-SI-1 | 11 | 6 | 116 | 14 |
| 8-SI-2 | 3 | 4 | 81 | 10 |
| 9-SI-1 | 4 | 5 | 158 | 20 |
| 9-SI-2 | 17 | 3 | 154 | 21 |
| V11 | 8 | 7 | 59 | 13 |
| V12 | 3 | 3 | 32 | 13 |
| V13 | 3 | 4 | 140 | 9 |
| V14 | 4 | 7 | 91 | 10 |

The results from the enzyme and proliferation assays do not show any systematic superiority of the compounds according to the invention relative to the compounds of the prior art.

Comparison In-vivo

The in-vivo efficacy of example 5-SI-2 was investigated in example 11 with V11 for comparison.
The in-vivo efficacy of example 6-SI-2 was investigated in example 12 with example 1.52 from WO 2005/037800 (=comparative substance V12) for comparison.
The in-vivo efficacy of example 2-SI-2 was investigated in example 13 with example 3.13 from WO 2005/037800 (=comparative substance V13) for comparison.
The in-vivo efficacy of example 1-SI-2 was investigated in example 14 with V14 for comparison.

EXAMPLE 11

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 $mm^2$. The study was terminated as soon as the tumors in one of the groups reached a size of approx. 150 $mm^2$.

The following test groups were used:
Group 1: Control, treatment with solubilizer (40% PEG400/ 60% water)
Group 2: Stereoisomer 2 prepared according to example 5 (=example 5-SI-2) 5 mg/kg, oral, 2× daily on day 4, 5, 11, 12)

The study was designed for determining the initial response of a human cervical carcinoma xenograft model to treatments with example 5-SI-2. The growth-inhibiting effect of the compounds was tested in the HeLa-MaTu cervical tumor model as xenograft on NMRI nude mice. Example 5-SI-2 was dissolved completely in the solubilizer 40% polyethylene glycol (PEG) 400/60% water to a final concentration of 0.5 mg/ml. Treatment of the established tumors was begun on day 4 after inoculation of the tumors. The study was terminated on day 17 after the tumor size in the animals in group 1 (control) had exceeded a size of approx. 150 mm$^2$.

The results from the studies (FIG. 1) show that example 5-SI-2 at the chosen dosage of 5 mg/kg oral in a cyclic treatment regimen (on 2 successive days 2× daily treatment followed by 5 treatment-free days) greatly inhibited tumor growth (group 3, reduction of tumor weight at the end of the study to 7% of the control group, p<0.05).

5-Br Comparative Substance (=V11)

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm$^2$. The study was terminated as soon as the tumors in one of the groups reached a size of approx. 150 mm$^2$.

The following test groups were used:
Group 1: Control, treatment with solubilizer (30% HPβCD/70% water)
Group 2: Compound according to WO 2005/037800 prepared according to preparation V11 disclosed above (8 mg/kg, oral, 2× daily on day 4, 5, 11, 12)

The study was designed for determining the initial response of a human cervical carcinoma xenograft model to treatments with the 5-Br comparative substance V11. The growth-inhibiting effect of the compounds was tested in the HeLa-MaTu cervical tumor model as xenograft on NMRI nude mice. V11 was dissolved completely in the solubilizer 30% β-hydroxypropyl-cyclodextrin (HPβCD)/70% water to a final concentration of 0.8 mg/ml. Treatment of the established tumors was begun on day 4 after inoculation of the tumors. The study was terminated on day 17 after the tumor size in the animals in group 1 (control) had exceeded a size of approx. 150 mm$^2$. The results from the studies (FIG. 2) show that V11, at the chosen dosage of 8 mg/kg oral 2× daily on 2 successive days followed by 5 treatment-free days, inhibited tumor growth in the HeLa-MaTu xenograft model (group 2, reduction of tumor weight at the end of the study to 39% of the control group, p<0.05).

Conclusion

Stereoisomer 2 of example 5 (example 5-SI-2 (5-CF$_3$)) achieves, in the cyclic treatment regimen consisting of two daily oral applications with a dose of 5 mg/kg on two successive days followed by 5 treatment-free days, complete inhibition of tumor growth in the HeLa-MaTu xenograft model (treatment/control ratio T/C=0.07). In the corresponding well-tolerated, cyclic treatment regimen at a dose of 8 mg/kg, the 5-Br comparative substance (=V11) only achieves a retardation of tumor growth in the HeLa-MaTu xenograft model (treatment/control ratio T/C=0.39). Surprisingly, in comparison with V11 (5-Br), example 5-SI-2 (5-CF$_3$) shows a higher potency (5 mg/kg dose for example 5-SI-2 compared with 8 mg/kg for V11) and far better antitumor efficacy (complete inhibition of tumor growth with a T/C=0.07 for example 5-SI-2 in comparison with slowing of tumor growth with a T/C=0.39 for V11).

EXAMPLE 12

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm$^2$. The study was terminated as soon as the tumors in one of the groups reached a size of approx. 150 mm$^2$.

is The following test groups were used:
Group 1: Control, treatment with solubilizer (40% PEG 400/60% water)
Group 2: Stereoisomer 2 prepared according to example 6 (=example 6-SI-2) (3 mg/kg, oral, 2× daily on day 4, 5, 11, 12, 17, 18)
Group 3: Stereoisomer 2 prepared according to example 6 (=example 6-SI-2) (4 mg/kg, oral, 2× daily on day 4, 5, 11, 12, 17, 18)
Group 4: Stereoisomer 2 prepared according to example 6 (=example 6-SI-2) (5 mg/kg, oral, 2× daily on day 4, 5, 11, 12, 17, 18)

The study was designed for determining the initial response of a human cervical carcinoma xenograft model to treatments with example 6-SI-2. The growth-inhibiting effect of the compounds was tested in the HeLa-MaTu cervical tumor model as xenograft on NMRI nude mice. Example 6-SI-2 was dissolved completely in the solubilizer 40% polyethylene glycol 400 (PEG 400)/60% water to a final concentration of 0.3 mg/ml (group 2), 0.4 mg/ml (group 3), or 0.5 mg/ml (group 4). Treatment of the established tumors was begun on day 4 after inoculation of the tumors. The study was terminated on day 20 after the tumor size in the animals in group 1 (control) had exceeded a size of approx. 150 mm$^2$.

The results from the studies (FIG. 3) show that in a treatment regimen consisting of two daily oral applications on 2 successive days followed by 5 treatment-free days, example 6-SI-2 provided dose-dependent inhibition of tumor growth in the HeLa-MaTu xenograft model. In the highest dose group (group 4), tumor growth is inhibited almost completely and a reduction of tumor weight at the end of the study to 8% of the control group is achieved (T/C=0.08, p<0.05).

5-Br Comparative Substance (=V12)

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm$^2$. The study was terminated as soon as the tumors in one of the groups reached a size of approx. 150 mm$^2$.

The following test groups were used:
Group 1: Control, treatment with solubilizer (40% PEG 400/60% water)
Group 2: Compound according to example 1.52 from WO 2005/037800 (=V12) (7 mg/kg, oral, 2× daily on day 4, 5, 11, 12, 17, 18, 23, 24)
Group 3: Compound according to example 1.52 from WO 2005/037800 (=V12) (8.5 mg/kg, oral, 2× daily on day 4, 5, 11, 12, 17, 18, 23, 24)
Group 4: Compound according to example 1.52 from WO 2005/037800 (=V12) (10 mg/kg, oral, 2× daily on day 4, 5, 11, 12, 17, 18, 23, 24)

The study was designed for determining the initial response of a human cervical carcinoma xenograft model to treatments with the 5-Br comparative substance V12. The growth-inhibiting effect of the compounds was tested in the HeLa-MaTu cervical tumor model as xenograft on NMRI nude mice. V12 was dissolved completely in the solubilizer 40% polyethylene glycol 400 (PEG 400)/60% water to a final concentration of 0.7 mg/ml (group 2), 0.85 mg/ml (group 3), or 1.0 mg/ml (group 4). Treatment of the established tumors was begun on day 4 after inoculation of the tumors. The study was terminated on day 28 after the tumor size in the animals in group 1 (control) had exceeded a size of approx. 150 mm$^2$.

The results from the studies (FIG. 4) show that in a treatment regimen consisting of two daily oral applications on 2 successive days followed by 5 treatment-free days, V12 produced dose-dependent weak inhibition of tumor growth in the HeLa-MaTu xenograft model. In the highest dose group (group 4) tumor growth is inhibited to approximately half in comparison with the control group (T/C=0.51).

Conclusion:

In the cyclic treatment regimen consisting of two daily oral applications with a dose of 5 mg/kg on two successive days followed by 5 treatment-free days, stereoisomer 2 of example 6 (example 6-SI-2 (5-CF$_3$)) achieves almost complete inhibition of tumor growth in the HeLa-MaTu xenograft model (treatment/control ratio T/C=0.08). In the corresponding well-tolerated, cyclic treatment regimen at a dose of 10 mg/kg, the compound according to example 1.52 from WO 2005/037800 (=V12 (5-Br)) only to achieves retardation of tumor growth in the HeLa-MaTu xenograft model (treatment/control ratio T/C=0.51). Surprisingly, in comparison with V12 (5-Br), example 6-SI-2 (5-CF$_3$) showed a higher potency (5 mg/kg dose for example 6-SI-2 in comparison with 10 mg/kg for V12) and far better antitumor efficacy (complete inhibition of tumor growth with a T/C=0.08 for example 6-SI-2 in comparison with is slowing of tumor growth with a T/C=0.51 for V12).

EXAMPLE 13

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm$^2$. The study was terminated as soon as the tumors in one of the groups reached a size of approx. 160 mm$^2$.

The following test groups were used:
Group 1: Control, treatment with solubilizer (40% PEG 400/60% water)
Group 2: Stereoisomer 2 prepared according to example 2 (=example 2-SI-2) (1.5 mg/kg, oral, 2× daily on day 5, 6, 12, 13, 19, 20)
Group 3: Stereoisomer 2 prepared according to example 2 (=example 2-SI-2) (2.0 mg/kg, oral, 2× daily on day 5, 6, 12, 13, 19, 20)
Group 4: Stereoisomer 2 prepared according to example 2 (=example 2-SI-2) (2.5 mg/kg, oral, 2× daily on day 5, 6, 12, 13, 19, 20)

The study was designed for determining the initial response of a human cervical carcinoma xenograft model to treatments with example 2-SI-2. The growth-inhibiting effect of the compounds was tested in the HeLa-MaTu cervical tumor model as xenograft on NMRI nude mice. Example 2-SI-2 was dissolved completely in the solubilizer 40% polyethylene glycol 400 (PEG 400)/60% water to a final concentration of 0.15 mg/ml (group 2), 0.2 mg/ml (group 3), or 0.25 mg/ml (group 4). Treatment of the established tumors was begun on day 5 after inoculation of the tumors. The study was terminated on day 20 after the tumor size in the animals in group 1 (control) had exceeded a size of approx. 160 mm$^2$.

The results from the studies (FIG. 5) show that in a treatment regimen consisting of two daily oral applications on 2 successive days followed by 5 treatment-free days, example 2-SI-2 produced dose-dependent inhibition of tumor growth in the HeLa-MaTu xenograft model. In the highest dose group (2.5 mg/kg, group 4), tumor growth is inhibited almost completely and there is reduction of tumor weight at the end of the study to 18% of the control group (T/C=0.18, p<0.05).

5-Br Comparative Substance (=V13)

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm$^2$. The study was terminated as soon as the tumors in one of the groups reached a size of approx. 160 mm$^2$.

The following test groups were used:
Group 1: Control, treatment with solubilizer (40% PEG 400/60% water)
Group 2: Compound according to example 3.13 from WO 2005/037800 (=V13) (6 mg/kg, oral, 2× daily on day 5, 6, 12, 13, 19, 20)
Group 3: Compound according to example 3.13 from WO 2005/037800 (=V13) (8 mg/kg, oral, 2× daily on day 5, 6, 12, 13, 19, 20)
Group 4: Compound according to example 3.13 from WO 2005/037800 (=V13) (10 mg/kg, oral, 2× daily on day 5, 6, 12, 13, 19, 20)

The study was designed for determining the initial response of a human cervical carcinoma xenograft model to treatments with the 5-Br comparative substance V13. The growth-inhibiting effect of the compounds was tested in the HeLa-MaTu cervical tumor model as xenograft on NMRI nude mice. V13 was dissolved completely in the solubilizer 40% polyethylene glycol 400 (PEG 400)/60% water to a final concentration of 0.6 mg/ml (group 2), 0.8 mg/ml (group 3), or 1.0 mg/ml (group 4). Treatment of the established tumors was begun on day 5 after inoculation of the tumors. The study was terminated on day 20 after the tumor size in the animals in group 1 (control) had exceeded a size of approx. 160 mm$^2$.

The results from the studies (FIG. 6) show that in a treatment regimen consisting of two daily oral applications on 2 successive days followed by 5 treatment-free days, V13 produced dose-dependent inhibition of tumor growth in the HeLa-MaTu xenograft model. In the highest dose group (10 mg/kg, group 4), tumor growth is inhibited very markedly and a reduction of tumor weight at the end of the study to 23% of the control group is achieved (T/C=0.23, p<0.05).

Conclusion:

In the cyclic treatment regimen consisting of two daily oral applications with a dose of 2.5 mg/kg on two successive days followed by 5 treatment-free days, stereoisomer 2 of example 2 (example 2-SI-2 (5-CF$_3$)) achieved almost complete inhibition of tumor growth in the HeLa-MaTu xenograft model (treatment/control ratio T/C=0.18). In the corresponding well-tolerated, cyclic treatment regimen at a dose of 10 mg/kg, the compound according to example 3.13 from WO 2005/037800 (=V13 (5-Br)) achieved slightly less retardation of tumor growth in the HeLa-MaTu xenograft model (treatment/control ratio T/C=0.23). Surprisingly, compared with V13 (5-Br), example 2-SI-2 (5-CF$_3$) showed a far higher potency (2.5 mg/kg dose for example 2-SI-2 in comparison with 10 mg/kg for V13) and a somewhat better antitumor efficacy (tumor growth inhibition with a T/C=0.18 for example 2-SI-2 in comparison with tumor growth inhibition with a T/C=0.23 for V13).

EXAMPLE 14

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm². The study was terminated as soon as the tumors in one of the groups reached a size of approx. 160 mm².

The following test groups were used:
Group 1: Control, treatment with solubilizer (40% PEG 400/ 60% water)
Group 2: Stereoisomer 2 prepared according to example 1 (=example 1-SI-2) (1.5 mg/kg, oral, 2× daily on day 5, 6, 12, 13, 19, 20)
Group 3: Stereoisomer 2 prepared according to example 1 (=example 1-SI-2) (2.0 mg/kg, oral, 2× daily on day 5, 6, 12, 13, 19, 20)
Group 4: Stereoisomer 2 prepared according to example 1 (=example 1-SI-2) (2.5 mg/kg, oral, 2× daily on day 5, 6, 12, 13, 19, 20)

The study was designed for determining the initial response of a human cervical carcinoma xenograft model to treatments with example 1-SI-2. The growth-inhibiting effect of the compounds was tested in the HeLa-MaTu cervical tumor model as xenograft on NMRI nude mice. Example 1-SI-2 was dissolved completely in the solubilizer 40% polyethylene glycol 400 (PEG 400)/60% water to a final concentration of 0.15 mg/ml (group 2), 0.2 mg/ml (group 3), or 0.25 mg/ml (group 4). Treatment of the established tumors was begun on day 5 after inoculation of the tumors. The study was terminated on day 20 after the tumor size in the animals in group 1 (control) had exceeded a size of approx. 160 mm².

The results from the studies (FIG. 7) show that in a treatment regimen consisting of two daily oral applications on 2 successive days followed by 5 treatment-free days, example 1-SI-2 produced dose-dependent inhibition of tumor growth in the HeLa-MaTu xenograft model. In the highest dose group (2.5 mg/kg, group 4), tumor growth is inhibited almost completely and a reduction of tumor weight at the end of the study to 19% of the control group is achieved (T/C=0.19, p<0.05).

5-Br Comparative Substance (=V14)

HeLa-MaTu (EPO-GmbH, Berlin) human cervical carcinoma cells, which were grown in cell culture, were implanted subcutaneously in the flank of female NMRI nude mice. The treatment was started as soon as the tumors had grown to a size of approx. 20 mm². The study was terminated as soon as the tumors in one of the groups reached a size of approx. 160 mm².

The following test groups were used:
Group 1: Control, treatment with solubilizer (40% PEG 400/ 60% water)
Group 2: Compound according to WO 2005/037800 prepared according to preparation V14 disclosed above (6 mg/kg, oral, 2× daily on day 5, 6, 12, 13, 19, 20)
Group 3: Compound according to WO 2005/037800 prepared according to preparation V14 disclosed above (8 mg/kg, oral, 2× daily on day 5, 6, 12, 13, 19, 20)
Group 4: Compound according to WO 2005/037800 prepared according to preparation V14 disclosed above (10 mg/kg, oral, 2× daily on day 5, 6, 12, 13, 19, 20)

The study was designed for determining the initial response of a human cervical carcinoma xenograft model to treatments with the 5-Br comparative substance V14. The growth-inhibiting effect of the compounds was tested in the HeLa-MaTu cervical tumor model as xenograft on NMRI nude mice. V14 was dissolved completely in the solubilizer 40% polyethylene glycol 400 (PEG 400)/60% water to a final concentration of 0.6 mg/ml (group 2), 0.8 mg/ml (group 3), or 1.0 mg/ml (group 4). Treatment of the established tumors was begun on day 5 after inoculation of the tumors. The study was terminated on day 20 after the tumor size in the animals in group 1 (control) had exceeded a size of approx. 160 mm².

The results from the studies (FIG. 8) show that in a treatment regimen consisting of two daily oral applications on 2 successive days followed by 5 treatment-free days, V14 produced dose-dependent inhibition of tumor growth in the HeLa-MaTu xenograft model. In the highest dose group (10 mg/kg, group 4), tumor growth is weakly inhibited and a reduction of tumor weight at the end of the study to 44% of the control group is achieved (T/C=0.44, statistical significance was not achieved).

Conclusion:

In the cyclic treatment regimen consisting of two daily oral applications with a dose of 2.5 mg/kg on two successive days followed by 5 treatment-free days, stereoisomer 2 of example 1 (example 1-SI-2 (5-CF$_3$)) achieved almost complete inhibition of tumor growth in the HeLa-MaTu xenograft model (treatment/control ratio T/C=0.19). In the corresponding well-tolerated, cyclic treatment regimen at a dose of 10 mg/kg, the 5-Br compound according to WO 2005/037800 (=V14 (5-Br)) achieved weak tumor growth inhibition in the HeLa-MaTu xenograft model (treatment/control ratio T/C=0.44). Surprisingly, compared with V14 (5-Br), example 1-SI-2 (5-CF$_3$) showed a far higher potency (2.5 mg/kg dose for example 1-SI-2 in comparison with 10 mg/kg for V14) and far superior antitumor efficacy (tumor growth inhibition with a T/C=0.19 for example 1-SI-2 in comparison with tumor growth inhibition with a T/C=0.44 for V14).

Figure 1:
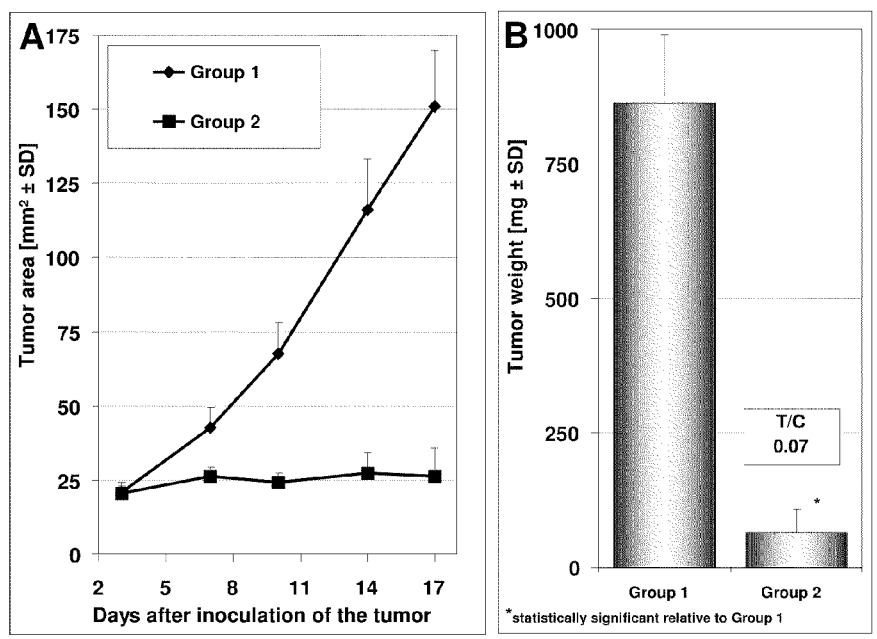
FIG. 1 shows the inhibition of tumor growth in the human HeLa-MaTu cervical tumor xenograft model during treatment with example 5-SI-2. HeLa-MaTu cells were implanted subcutaneously in NMRI nude mice on day 0. The treatment started on day 4 after the tumors had reached a size of approx. 20 mm². The treatments were carried out with the following dosages and application regimens:
Group 1: (Control group)—solubilizer (40% PEG400/ 60% water)
Group 2: Example 5-SI-2, cyclic treatment regimen, 2× daily, oral, on days 4, 5, 11, 12, dosage 5 mg/kg.
A) growth of the HeLa-MaTu xenograft tumors as a function of time.
B) weight of the HeLa-MaTu tumors on day 17, and ratio of the average tumor weight in the treatment group to the average tumor weight in the control group (T/C).
Figure 2:
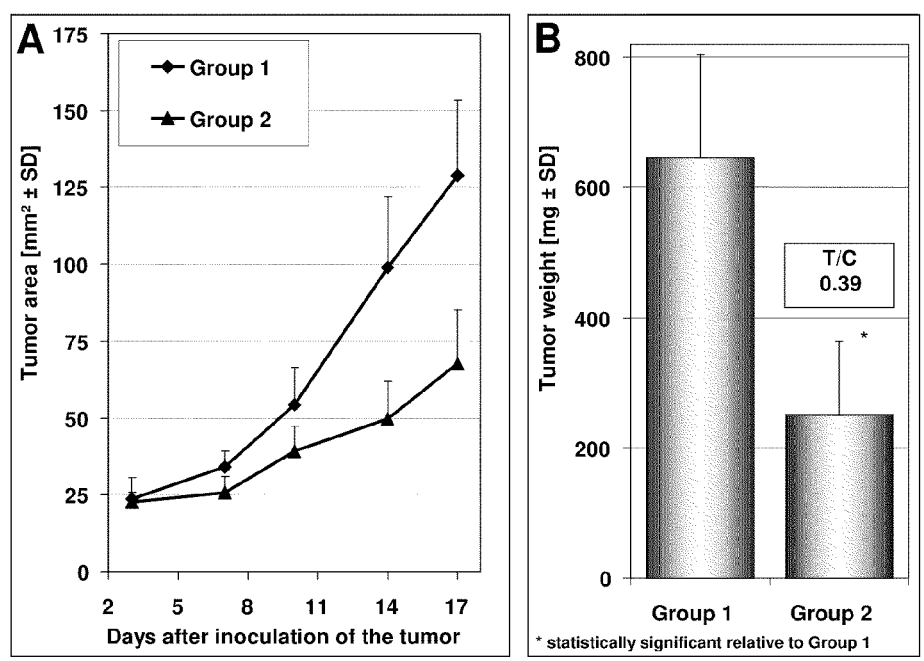
FIG. 2 shows the inhibition of tumor growth in the human HeLa-MaTu cervical tumor xenograft model during treatment with V11. HeLa-MaTu cells were implanted subcutaneously in NMRI nude mice on day 0. The treatment started on day 4 after the tumors had reached a size of approx. 20 mm². The treatments were carried out with the following dosages and application regimens:
Group 1: (Control group)—solubilizer (30% HPβCD/70% water, 1× daily oral on day 4-17);
Group 2: V11, cyclic treatment regimen, 2× daily oral on days 4, 5, 11, 12, dosage 8 mg/kg.
A) growth of the HeLa-MaTu xenograft tumors as a function of time.
B) weight of the HeLa-MaTu tumors on day 17, and ratio of the average tumor weight in the respective treatment groups to the average tumor weight in the control group (T/C).
Figure 3:
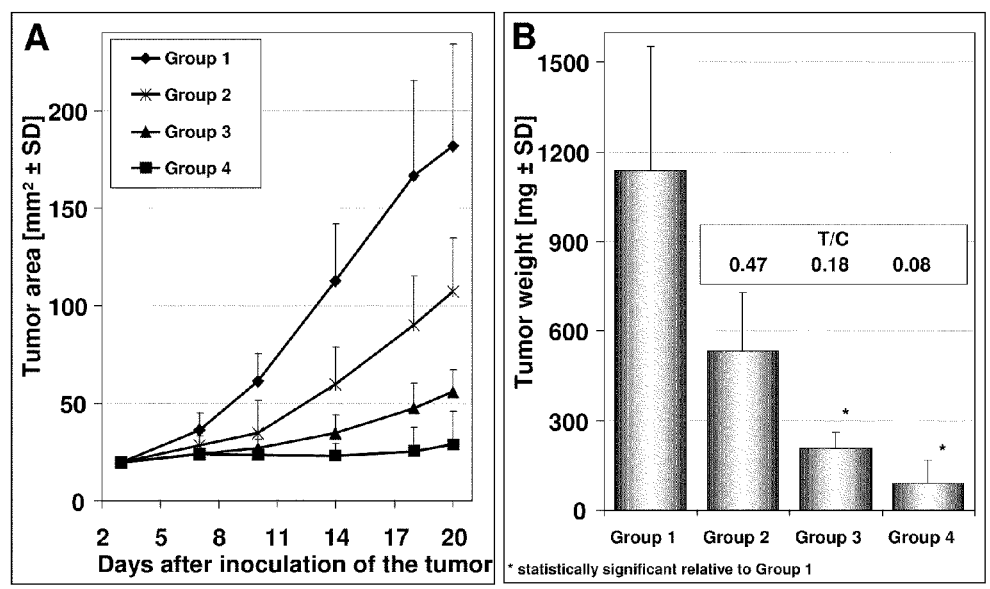
FIG. 3: shows the inhibition of tumor growth in the human HeLa-MaTu cervical tumor xenograft model during treatment with example 6-SI-2. HeLa-MaTu cells were implanted subcutaneously in NMRI nude mice on day 0. The treatment started on day 4 after the tumors had reached a size of approx. 20 mm². The treatments were carried out at the following dosages and in a cyclic treatment regimen consisting of two daily oral applications on days 4, 5, 11, 12, 17, and 18:
- Group 1: (Control group)—solubilizer (40% PEG400/60% water);
- Group 2: Example 6-SI-2, dosage 3 mg/kg;
- Group 3: Example 6-SI-2, dosage 4 mg/kg;
- Group 4: Example 6-SI-2, dosage 5 mg/kg.
  A) growth of the HeLa-MaTu xenograft tumors as a function of time.
  B) weight of the HeLa-MaTu tumors on day 20, and ratio of the average tumor weight in the respective treatment groups to the average tumor weight in the control group (T/C).
Figure 4:
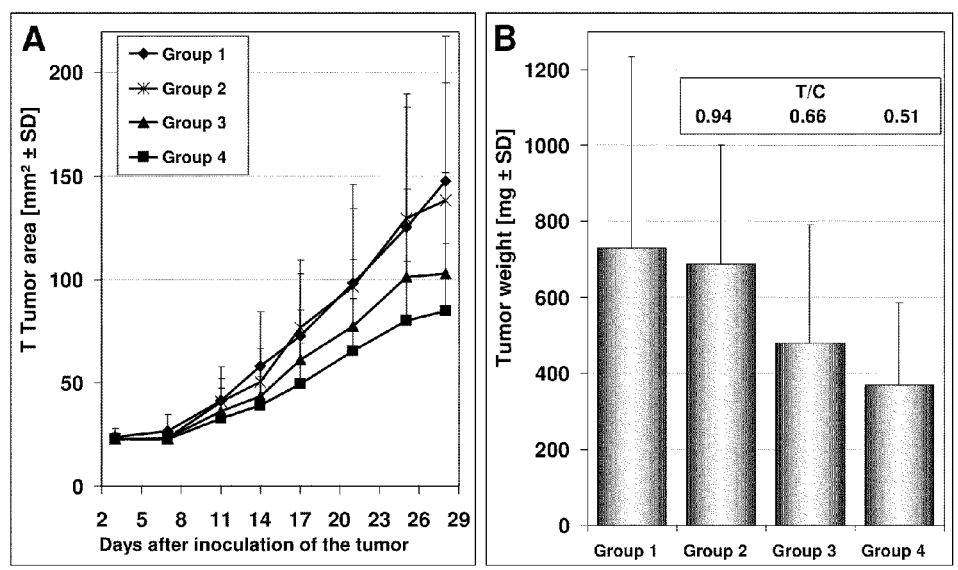
FIG. 4: shows the inhibition of tumor growth in the human HeLa-MaTu cervical tumor xenograft model during treatment with V12. HeLa-MaTu cells were implanted subcutaneously in NMRI nude mice on day 0. The treatment started on day 4 after the tumors had reached a size of approx. 20 mm². The treatments were carried out at the following dosages and in a cyclic treatment regimen consisting of two daily oral applications on days 4, 5, 11, 12, 17, 18, 23 and 24:
- Group 1: (Control group) - solubilizer (40% PEG400/60% water);
- Group 2: V12, dosage 7 mg/kg;
- Group 3: V12, dosage 8.5 mg/kg;
- Group 4: V12, dosage 10 mg/kg.
  A) growth of the HeLa-MaTu xenograft tumors as a function of time.
  B) weight of the HeLa-MaTu tumors on day 28, and ratio of the average tumor weight in the respective treatment groups to the average tumor weight in the control group (T/C).
Figure 5:
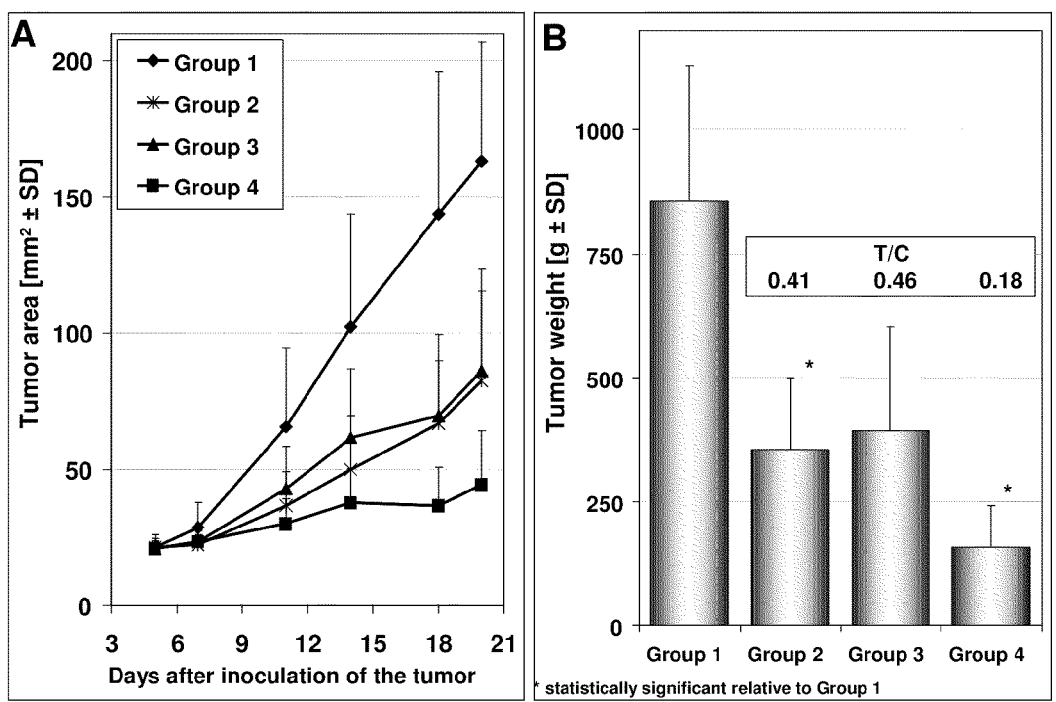
FIG. 5: shows the inhibition of tumor growth in the human HeLa-MaTu cervical tumor xenograft model during treatment with example 2-SI-2. HeLa-MaTu cells were implanted subcutaneously in NMRI nude mice on day 0. The treatment started on day 5 after the tumors had reached a size of approx. 20 mm². The treatments were carried out at the following dosages and in a cyclic treatment regimen consisting of two daily oral applications on days 5, 6, 12, 13, 19, and 20:
- Group 1:(Control group)—solubilizer (40% PEG400/60% water);
- Group 2: Example 2-SI-2, dosage 1.5 mg/kg;
- Group 3: Example 2-5I-2, dosage 2 mg/kg;
- Group 4: Example 2-SI-2, dosage 2.5 mg/kg.
  A) growth of the HeLa-MaTu xenograft tumors as a function of time.
  B) weight of the HeLa-MaTu tumors on day 20, and ratio of the average tumor weight in the respective treatment groups to the average tumor weight in the control group (T/C).
Figure 6:
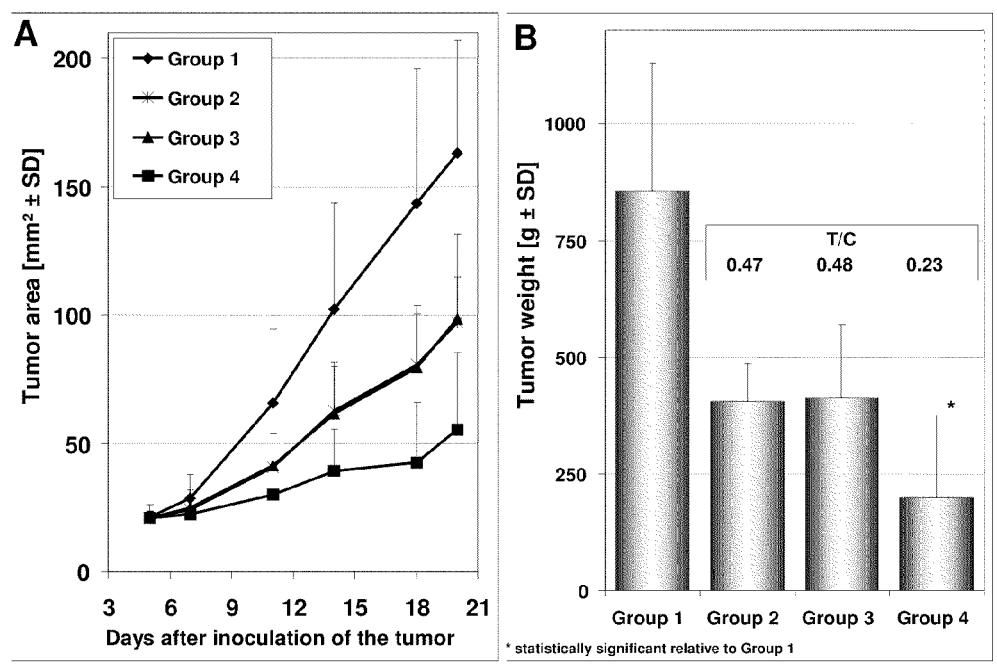
FIG. 6: shows the inhibition of tumor growth in the human HeLa-MaTu cervical tumor xenograft model during treatment with V13. HeLa-MaTu cells were implanted subcutaneously in NMRI nude mice on day 0. The treatment started on day 5 after the tumors had reached a size of approx. 20 mm². The treatments were carried out at the following dosages and in a cyclic treatment regimen consisting of two daily oral applications on days 5, 6, 12, 13, 19, and 20:
- Group 1: (Control group)—solubilizer (40% PEG400/60% water);
- Group 2: V13, dosage 6 mg/kg;
- Group 3: V13, dosage 8 mg/kg;
- Group 4: V13, dosage 10 mg/kg.
  A) growth of the HeLa-MaTu xenograft tumors as a function of time.
  B) weight of the HeLa-MaTu tumors on day 20, and ratio of the average tumor weight in the respective treatment groups to the average tumor weight in the control group (T/C).
Figure 7:
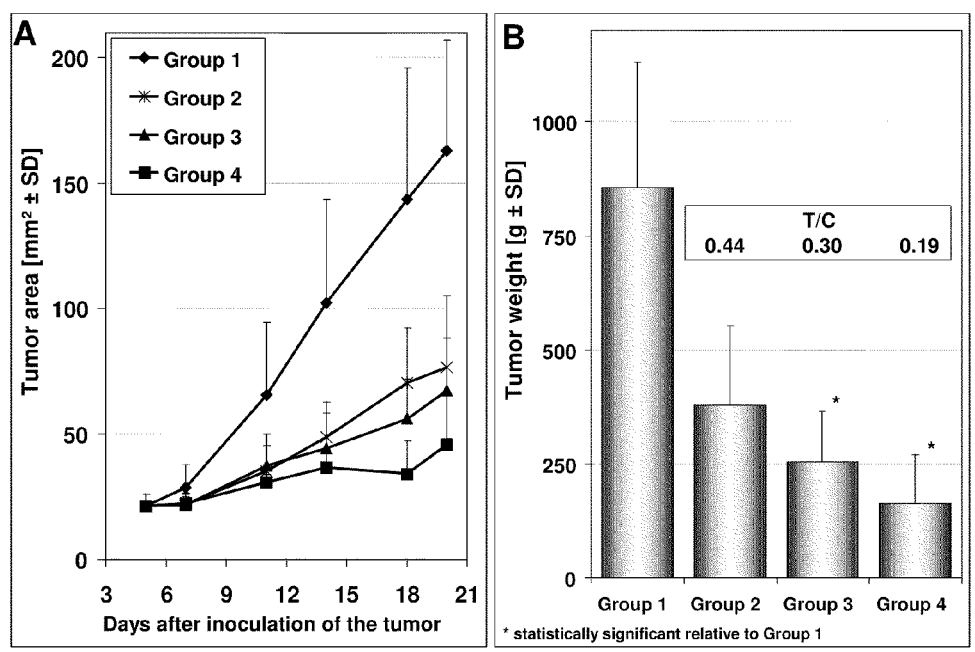
FIG. 7: shows the inhibition of tumor growth in the human HeLa-MaTu cervical tumor xenograft model during treatment with example 1-SI-2. HeLa-MaTu cells were implanted subcutaneously in NMRI nude mice on day 0. The treatment started on day 5 after the tumors had reached a size of approx. 20 mm². The treatments were carried out at the following dosages and in a cyclic treatment regimen consisting of two daily oral applications on days 5, 6, 12, 13, 19, and 20:
- Group 1:(Control group)—solubilizer (40% PEG400/60% water);
- Group 2: Example 1-SI-2, dosage 1.5 mg/kg;
- Group 3: Example 1-SI-2, dosage 2 mg/kg;
- Group 4: Example 1-SI-2, dosage 2.5 mg/kg.
  A) growth of the HeLa-MaTu xenograft tumors as a function of time.
  B) weight of the HeLa-MaTu tumors on day 20, and ratio of the average tumor weight in the respective treatment groups to the average tumor weight in the control group (T/C).
Figure 8:
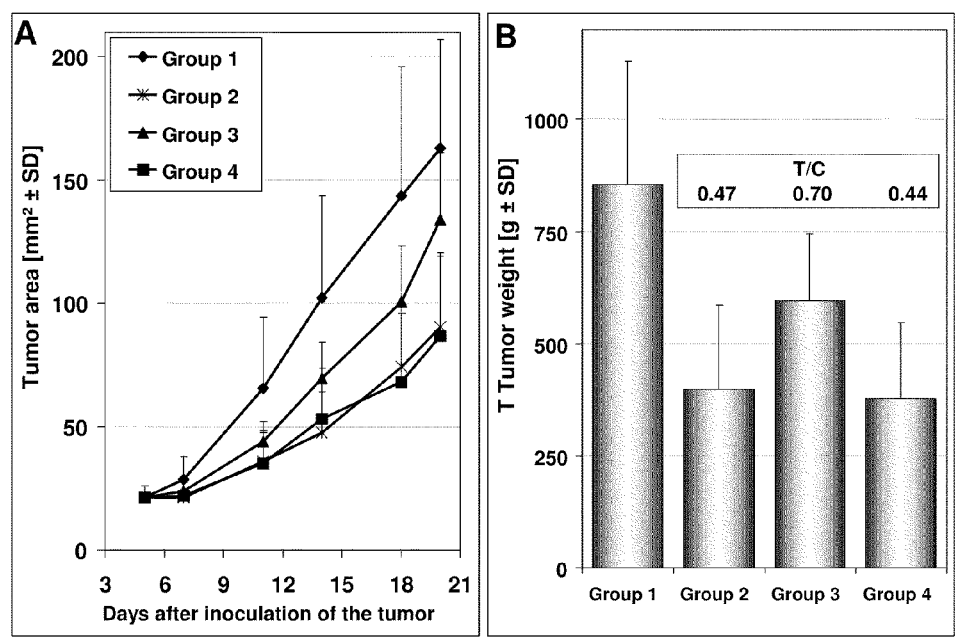
FIG. 8: shows the inhibition of tumor growth in the human HeLa-MaTu cervical tumor xenograft model during treatment with V14. HeLa-MaTu cells were implanted subcutaneously in NMRI nude mice on day 0. The treatment started on day 5 after the tumors had reached a size of approx. 20 mm². The treatments were carried out at the following dosages and in a cyclic treatment regimen consisting of two daily oral applications on days 5, 6, 12, 13, 19, and 20:
- Group 1: (Control group)—solubilizer (40% PEG400/60% water);
- Group 2: V14, dosage 6 mg/kg;
- Group 3: V14, dosage 8 mg/kg;
- Group 4: V14, dosage 10 mg/kg.
  A) growth of the HeLa-MaTu xenograft tumors as a function of time.
  B) weight of the HeLa-MaTu tumors on day 20, and ratio of the average tumor weight in the respective treatment groups to the average tumor weight in the control group (T/C).

The invention claimed is:

1. Compounds of general formula (I)

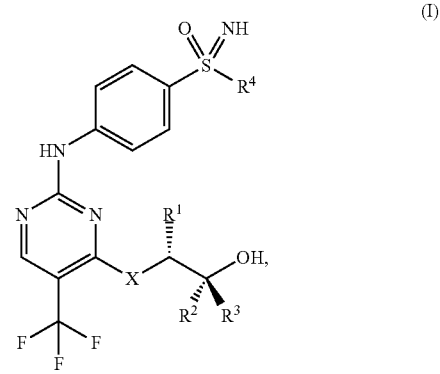

in which
X stands for —O— or —NH—, and
$R^1$ stands for a methyl, ethyl, propyl or isopropyl group, and R² and R³ independently of one another, stand for hydrogen, a methyl or ethyl group, and R⁴ stands for a $C_2$-$C_6$-alkyl group or a $C_3$-$C_7$-cycloalkyl ring, and salts, diastereomers and enantiomers thereof.

2. Compounds as claimed in claim 1,
characterized in that X stands for —O—,
and salts, diastereomers and enantiomers thereof.

3. The compounds as claimed in claim 1,
characterized in that R¹ stands for a methyl group,
and salts, diastereomers and enantiomers thereof.

4. The compounds as claimed in claim 1,
characterized in that R² stands for a methyl group,
and salts, diastereomers and enantiomers thereof.

5. The compounds as claimed in claim 1,
characterized in that R³ stands for hydrogen or a methyl group,
and salts, diastereomers and enantiomers thereof.

6. The compounds as claimed in claim 1,
characterized in that R⁴ stands for a methyl or ethyl group or for a cyclopropyl ring,
and salts, diastereomers and enantiomers thereof.

7. The compounds of general formula (I) as claimed in claim 1, in which
X stands for —O— or —NH—, and
R¹ stands for a methyl group, and
R² stands for a methyl group, and
R³ stands for hydrogen or a methyl group, and
R⁴ stands for a methyl or ethyl group or for a cyclopropyl ring,
and salts, diastereomers and enantiomers thereof.

8. A method of production of compounds of general formula (Ia), comprising at least one of steps a)-h)

a) Oxidation of a compound of formula (IVd)

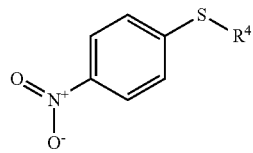
(IVd)

to the sulfoxide of formula (IVc)

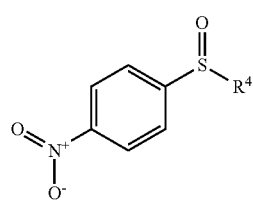
(IVc)

b₁) Direct imination of the sulfoxide of formula (IVc)

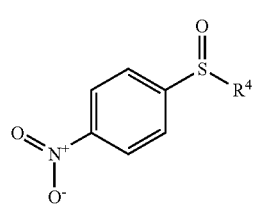
(IVc)

to a protected sulfoximine of formula (IVa)

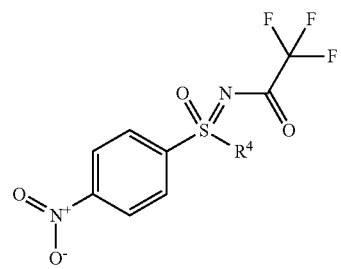
(IVa)

or b₂) Imination of the sulfoxide of formula (IVc)

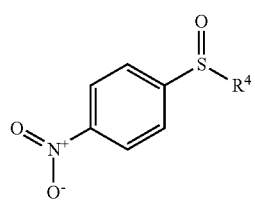
(IVc)

to an unprotected sulfoximine of formula (IVb)

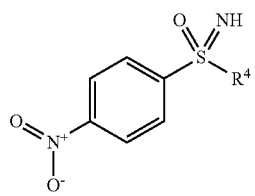
(IVb)

and subsequent introduction of the protective group to a compound of formula (IVa)

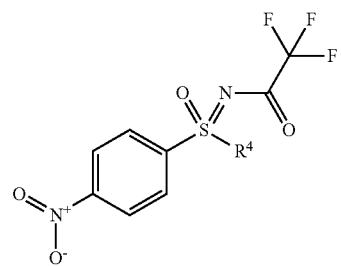
(IVa)

c) Reduction of the compound of formula (IVa)

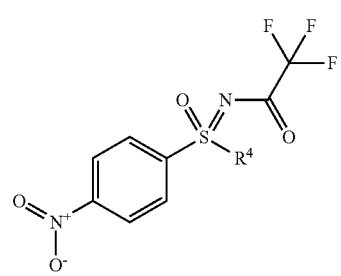
(IVa)

to a compound of formula (IV)

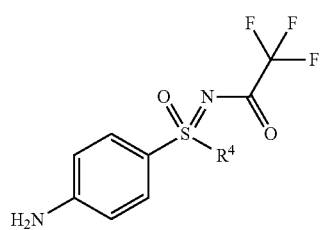

(IV)

d) Functionalization of the 4-position of 2,4-dichloro-5-iodo-pyrimidine (VII)

(VII)

by reaction with a mono-protected diol of formula (VI)

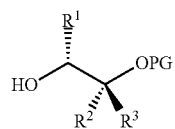

(VI)

with formation of an intermediate of formula (Va)

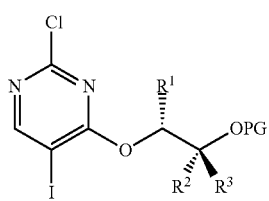

(Va)

e) Production of the 5-CF3 intermediate (V)

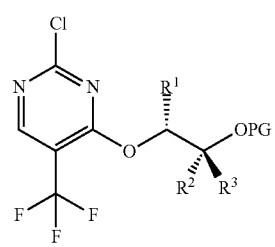

(V)

from the 5-I intermediate (Va)

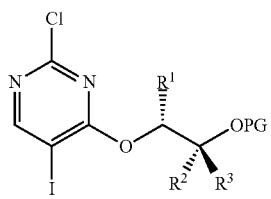

(Va)

f) Coupling of the compounds of formula (IV)

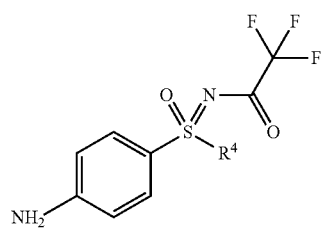

(IV)

and (V)

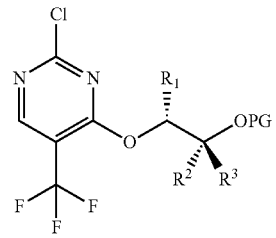

(V)

to form the intermediate of formula (III)

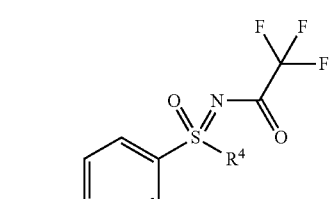

(III)

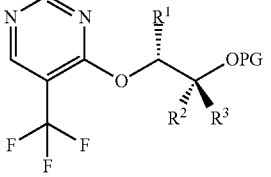

g) Cleavage of the protective group PG of a compound of formula (III)

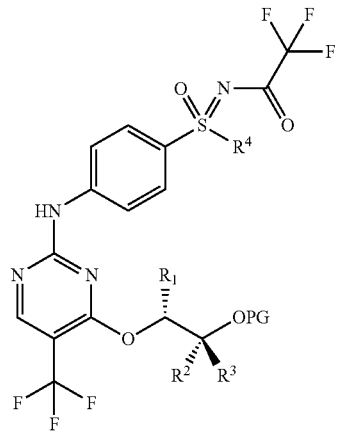
(III)

with formation of (II)

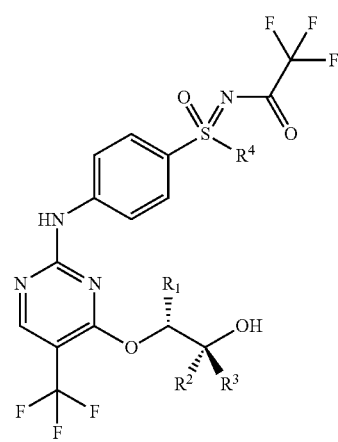
(II)

h) Cleavage of the protective group on the sulfoximine of formula (II)

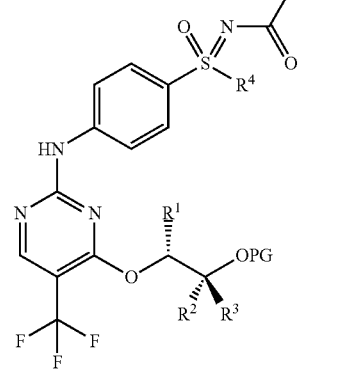
(II)

with formation of (Ia)

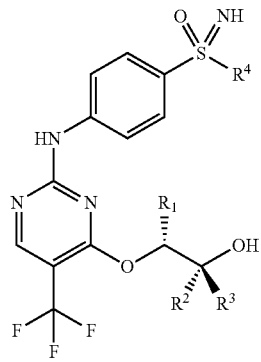
(Ia)

characterized in that the substituents $R^1$, $R^2$, $R^3$ and $R^4$ have the meanings given in general formula (I) of claim 1.

9. A method of production of compounds of general formula (Ib), comprising at least one of steps a)-f)

a) Oxidation of a compound of formula (IVd)

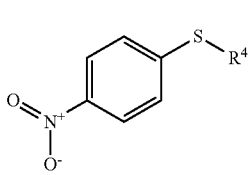
(IVd)

to the sulfoxide of formula (IVc)

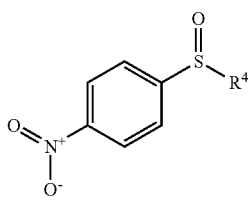
(IVc)

$b_1$) Direct imination of the sulfoxide of formula (IVc)

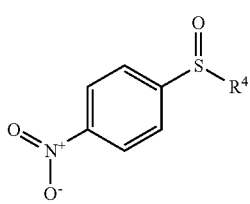
(IVc)

to form a protected sulfoximine of formula (IVa)

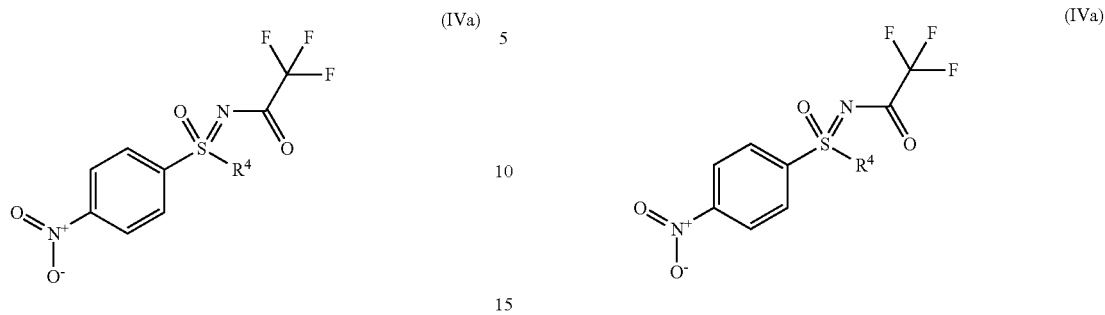

or b₂) Imination of the sulfoxide of formula (IVc)

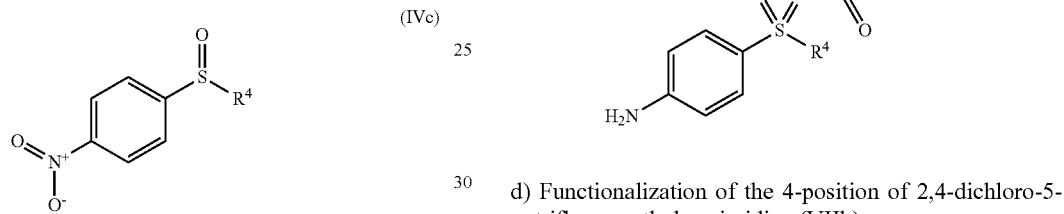

to form an unprotected sulfoximine of formula (IVb)

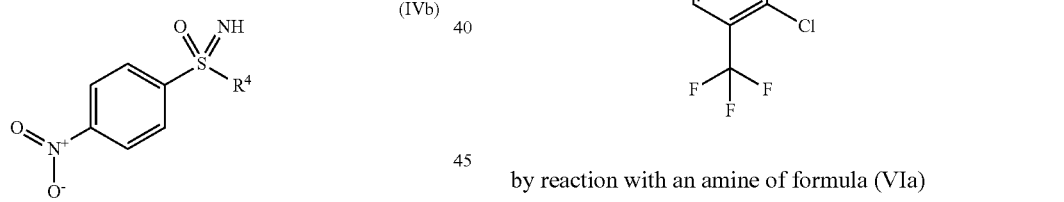

and subsequent introduction of the protective group to a compound of formula (IVa)

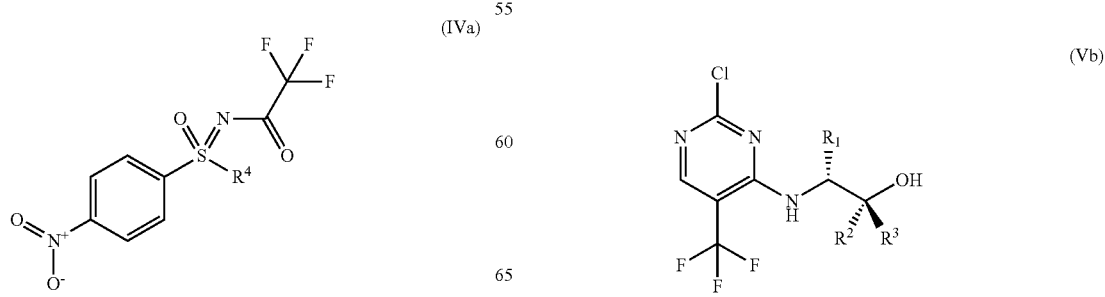

c) Reduction of the compound of formula (IVa)

(IVa)

to a compound of formula (IV)

(IV)

d) Functionalization of the 4-position of 2,4-dichloro-5-trifluoromethyl-pyrimidine (VIIb)

(VIIb)

by reaction with an amine of formula (VIa)

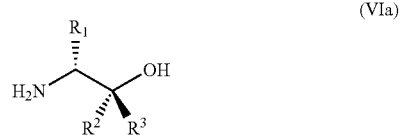

with formation of an intermediate of formula (Vb)

(Vb)

e) Coupling of the compounds of formula (Vb)

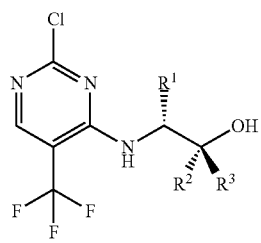
(Vb)

and (IV)

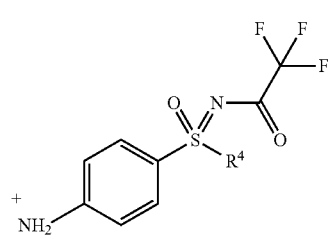
(IV)

to form the intermediate of formula (IIb)

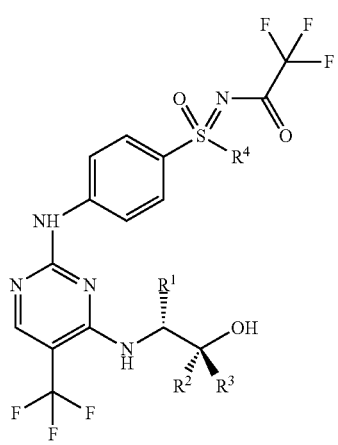
(IIb)

f) Cleavage of the protective group on the sulfoximine of formula (IIb)

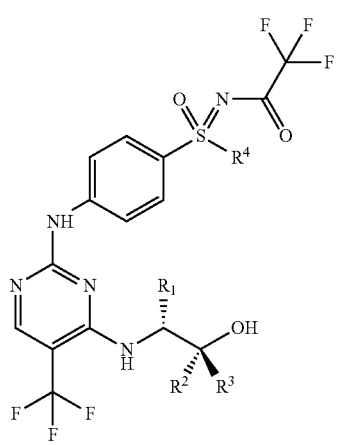
(IIb)

with formation of (Ib)

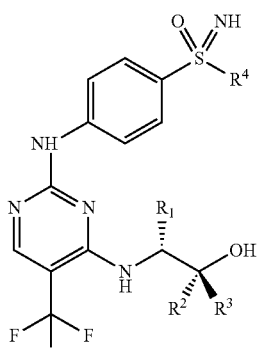
(Ib)

characterized in that the substituents $R^1$, $R^2$, $R^3$ and $R^4$ have the meanings given in general formula (I) of claim 1.

10. The compounds as claimed in claim 1 for use as medicinal products.

11. A pharmaceutical formulation containing a compound as claimed in claim 1.

12. A method for treating cancer comprising administering an effective amount of a compound as claimed in claim 1 to a patient in need thereof.

13. A compound as claimed in claim 1, wherein the compound is (RS)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide.

14. A compound as claimed in claim 1, wherein the compound is (R)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide.

15. A compound as claimed in claim 1, wherein the compound is (S)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide.

16. The method as claimed in claim 12, wherein the cancer is cervical cancer.

17. The method as claimed in claim 16, wherein the compound is (RS)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide.

18. The method as claimed in claim 16, wherein the compound is (R)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide.

19. The method as claimed in claim 16, wherein the compound is (S)-S-Cyclopropyl-S-(4-{[4-{[(1R,2R)-2-hydroxy-1-methylpropyl]oxy}-5-(trifluoromethyl)pyrimidin-2-yl]amino}phenyl)sulfoximide.

* * * * *